| (12) | United States Patent | (10) Patent No.: | US 10,820,881 B2 |
|---|---|---|---|
| | Matthews et al. | (45) Date of Patent: | Nov. 3, 2020 |

(54) METHOD FOR ANALYZING AND CORRECTING MEASUREMENT VARIABILITY IN PET IMAGES

(71) Applicants: Dawn C. Matthews, Grayslake, IL (US); Ana S. Lukic, Chicago, IL (US); Boris Marendic, Chicago, IL (US); Randolph D. Andrews, McHenry, IL (US)

(72) Inventors: Dawn C. Matthews, Grayslake, IL (US); Ana S. Lukic, Chicago, IL (US); Boris Marendic, Chicago, IL (US); Randolph D. Andrews, McHenry, IL (US)

(73) Assignee: ADM DIAGNOSTICS, INC., Northbrook, IL (US)

( * ) Notice: Subject to any disclaimer, the term of this patent is extended or adjusted under 35 U.S.C. 154(b) by 1033 days.

(21) Appl. No.: 14/909,364

(22) PCT Filed: Aug. 4, 2014

(86) PCT No.: PCT/US2014/049565
§ 371 (c)(1),
(2) Date: Feb. 1, 2016

(87) PCT Pub. No.: WO2015/017851
PCT Pub. Date: Feb. 5, 2015

(65) Prior Publication Data
US 2016/0166229 A1 Jun. 16, 2016

Related U.S. Application Data

(60) Provisional application No. 61/861,677, filed on Aug. 2, 2013.

(51) Int. Cl.
*A61B 6/00* (2006.01)
*G06T 7/00* (2017.01)
(Continued)

(52) U.S. Cl.
CPC .............. *A61B 6/583* (2013.01); *A61B 6/037* (2013.01); *A61B 6/501* (2013.01); *A61B 6/5217* (2013.01);
(Continued)

(58) Field of Classification Search
CPC ....... A61B 6/583; A61B 6/5217; A61B 6/582; A61B 6/037; A61B 6/501; A61B 5/0035;
(Continued)

(56) References Cited

U.S. PATENT DOCUMENTS

| 5,027,817 A | 7/1991 | John |
| 8,233,689 B2 | 7/2012 | Razifar et al. |

(Continued)

FOREIGN PATENT DOCUMENTS

JP 2003-52685 A 2/2003

*Primary Examiner* — Amanda Lauritzen Moher
(74) *Attorney, Agent, or Firm* — Pauley Erickson & Swanson

(57) ABSTRACT

A computer-implemented method for correcting measurement variability across a scanner field of view within an image scan, such as in PET imaging. The method operates on a slice-by-slice application and identifies and negates scan inconsistencies across the scanner field of view by normalizing values across the image scan as a function of reference signals measured across the field of view.

22 Claims, 22 Drawing Sheets

(51) Int. Cl.
  G01T 1/166 (2006.01)
  A61B 6/03 (2006.01)
  G01T 7/00 (2006.01)
  A61B 5/00 (2006.01)
  G01B 15/00 (2006.01)
  G06T 11/00 (2006.01)

(52) U.S. Cl.
  CPC ............ A61B 6/582 (2013.01); G01T 1/1663 (2013.01); G01T 7/005 (2013.01); G06T 7/0014 (2013.01); A61B 5/00 (2013.01); A61B 5/0035 (2013.01); A61B 6/4258 (2013.01); A61B 6/504 (2013.01); A61B 6/5211 (2013.01); G01B 15/00 (2013.01); G06T 7/0012 (2013.01); G06T 11/005 (2013.01); G06T 11/008 (2013.01); G06T 2207/00 (2013.01); G06T 2207/10104 (2013.01); G06T 2207/10108 (2013.01); G06T 2207/20201 (2013.01)

(58) Field of Classification Search
  CPC ......... A61B 5/00; A61B 6/5211; A61B 6/504; A61B 6/4258; G01T 1/1663; G01T 7/005; G06T 7/0014; G06T 11/008; G06T 2207/20201; G06T 11/005; G06T 2207/00; G06T 2207/10108; G06T 2207/10104; G06T 7/0012; G01B 15/00
  See application file for complete search history.

(56) References Cited

U.S. PATENT DOCUMENTS

| | | | | |
|---|---|---|---|---|
| 2002/0042563 | A1* | 4/2002 | Becerra | A61B 5/055 600/407 |
| 2002/0163994 | A1* | 11/2002 | Jones | A61B 5/418 378/21 |
| 2005/0253074 | A1* | 11/2005 | Jones | G01T 1/2985 250/363.04 |
| 2007/0176087 | A1* | 8/2007 | Wang | G01T 1/1648 250/252.1 |
| 2009/0292551 | A1* | 11/2009 | Sirohey | G06F 19/321 705/2 |
| 2010/0249559 | A1 | 9/2010 | Lovejoy | |
| 2012/0128132 | A1* | 5/2012 | Coolens | A61B 6/583 378/207 |
| 2014/0200848 | A1* | 7/2014 | Panin | A61B 6/037 702/179 |
| 2016/0055633 | A1* | 2/2016 | Bertone | A61B 6/50 382/131 |

* cited by examiner

METHOD FOR ANALYZING AND CORRECTING MEASUREMENT VARIABILITY IN PET IMAGES

CROSS REFERENCE TO RELATED APPLICATION

This application is a National Phase entry of PCT/US2014/049565, filed on 4 Aug. 2014, which claims the benefit of U.S. Provisional Patent Application, Ser. No. 61/861,677, filed on 2 Aug. 2013. The co-pending PCT Application is hereby incorporated by reference herein in its entirety and is made a part hereof, including but not limited to those portions which specifically appear hereinafter.

FIELD OF THE INVENTION

This invention relates generally to scanning and imaging using imaging agents, such as radiotracers and, in particular, to determining and compensating for measurement variability across a scanner field of view, such as for use in PET or SPECT imaging of the brain.

BACKGROUND OF THE INVENTION

Positron emission tomography (PET) is an imaging technology that measures chemical or functional activity in the brain or other parts of the body by detecting gamma rays emitted by the decay of a radioactive tracer injected into the patient. The radiotracer is designed to bind to a target entity of interest, such as a neurotransmitter receptor, glucose, or the amyloid plaque or tau that build up in the brains of Alzheimer's disease (AD) patients. In the case of amyloid plaque, the greater the amount of plaque, the greater the binding of the tracer, and the greater and more expansive the signal intensity in the resulting image. (For further background on PET imaging, see Wernick M, ed., "Emission Tomography: The Fundamentals of PET and SPECT"; Schmidt M, Matthews D et al, "PET Imaging in Alzheimer's Disease", book chapter, "Translational Neuroimaging: Tools for CNS Drug Discovery, Development and Treatment," McArthur R ed., 2012, herein incorporated by reference). FIG. 1 shows a sample amyloid PET scan in transaxial and sagittal views. Amyloid tracers include 11C-PiB (Pittsburgh Compound B), florbetapir, flutemetamol, florbetaban, and others. Although amyloid preferentially accumulates in gray matter, most amyloid PET tracers also bind to white matter, either due to slower clearance of the tracer from white matter, non-specific binding to white matter, or speicific binding to a non-amyloid entity such as myelin. Hence, the intensity (dark gray) in FIG. 1 is a combination of white matter binding (around the ventricles in the middle of the brain) and binding to amyloid. While amyloid is used as an example for this invention, the same measurement variability issues, and the invention, apply to other tracers.

In brain imaging, the amount of tracer binding is often measured by taking the ratio of the mean intensity in a region of interest (ROI, or volume of interest, VOI, since typically multi-slice), such as the frontal cortex or anterior cingulate (structures of the brain) as compared to (divided by) the average intensity in another, reference region, also typically inclusive of a subset of tissue from several brain slices. This is called a Standardized Uptake Value Ratio (SUVR). FIG. 2 shows sample VOIs and a sample reference region (Gray Cerebellum) overlaid on an amyloid PET image. A "cortical average" is often calculated using four to six individual VOIs that are highly correlated, such as frontal, anterior and posterior cingulate, lateral temporal, and parietal regions.

One of the most critical factors affecting measurement is the selection and reliability of the reference region. The normalization of all other values to this reference means that variability in this region will impact all regions of interest measures for the scan, with the greatest impact upon measured SUVRs (Landau et al., 2013). Particularly in longitudinal studies, where measured changes may be of a few percent, variability in the reference region can overwhelm amyloid signal (or other signal of interest, such as glucose metabolism or tau) associated with treatment or disease progression. If unaddressed, statistical power will be reduced, increasing required study population size. Ideally, the reference region should remain stable from scan to scan (for example, not accumulate amyloid in the case of amyloid measurement), so that despite changes in the target region of interest due to amyloid accumulation or other physiologic changes, the reference provides a valid basis for comparison.

Cerebellar (gray) cortex has been used in the majority of amyloid studies due to its lack of amyloid accumulation in typical Alzheimer's Disease (Klunk et al., *Neuroimaging Clin N Am* 2003; Lopresti et al., 2005; Braak et al., 1991) and the goal of matching tracer clearance properties, which differ between gray and white tissue, to target cortical regions of interest (Price et al., 2005). It has also been used in other tracer measurements, such as those for dopamine receptors, glucose, and tau. However, variability arises from, for example, the cerebellum's low signal relative to sources of noise, proximity to the edge of the scanner FOV where noise and truncation can occur, and vulnerability to scatter effects. Signal levels vary from inferior to superior slices in cerebellar cortex, with the most inferior slices most prone to noise and inter-scanner variability, and measurements are susceptible to contamination by higher white matter values or low CSF values if head motion occurs. For these reasons, reference region definition may optimally exclude the most inferior and superior tissue slices and be eroded from neighboring tissue, and consistent boundaries, including any adjustment for a truncated scan, should be used for within-subject longitudinal comparisons. Whole cerebellum (including both gray and white tissue) has been proposed as a reference for tracers such as florbetapir due to slightly better differentiation of amyloid positive and negative controls (Clark et al., *JAMA*, 2011), higher signal intensity, inclusion of more central tissue that reduces vulnerability to edge or truncation effects, and match with target regions of interest that include both white and gray tissue components. The pons, which has high tracer affinity to its white matter tissue but is amyloid devoid (Thal et al., 2002), has been demonstrated as a possible alternate reference region for amyloid measurement with advantages of higher signal, less vulnerable position, and equivalent or superior effect size and variance in some cross sectional and longitudinal comparisons (Edison et al., *Neuroimage* 2012; Knight et al., *Brain*, 2011; other refs). It has also been used as a reference region for glucose metabolism measurement in Alzheimer's Disease due to its lower rate of activity decline during disease progression relative to other tissue (Minoshima et al, 1995). Measurement variance may arise due to its relatively small volume and sensitivity to rotational head motion. Subcortical white matter, which does not accumulate amyloid (Ikonomovic et al., 2008), has additionally been used as an alternate reference region for amyloid measurement (Wong K P et al., 2009; Wong D et al., 2010). Combinations of reference regions have also been proposed to offset variability in a single region.

However, despite the various approaches taken in reference region definition for amyloid imaging, measurement is plagued by noise and inconsistency across reference regions. For example, FIG. 3 is a plot of the percentage change between two scans, 24 months apart (resulting in a SUVR value in each case). Each point on the x-axis represents a different subject.

FIG. 4 shows the longitudinal trajectories of the "amyloid burden", or cortical average SUVRs of subjects with Mild Cognitive Impairment (MCI, often a precursor clinical state to AD dementia) imaged using 11C-PiB, with values posted by ADNI. Several subjects follow rather erratic patterns, increasing and then decreasing or vice versa, or exhibiting unexpectedly steep slopes or decreases. Thus, the issue of inconsistency is not specific to a single tracer.

The use of different scanner models can also cause differences in measured values for the same amyloid burden. FIG. 5 shows differences in the absolute and percent change in longitudinal SUVR for two different subjects who were each measured on one scanner model at baseline and a different scanner model 24 months later. It can be seen that while the SUVRs referenced to cerebellum show decreases (negative trajectories), those referenced to pons and other white matter (e.g. centrum ovale) are either positive or less negative.

As one final example, shown in FIG. 6 are average rates of change for 68 subjects who were imaged using florbetapir at a 24 month interval, in three groups. The three groups (strata) were determined by the subject's amyloid burden (cortical average SUVR value) at baseline—negative for amyloid, positive, and high positive. It can be seen that although the rates for the middle group are consistent across reference regions (those with baseline amyloid values that were positive but not in the highest category), directionality varies across reference regions for those who were amyloid negative (low amyloid values) or high positive at baseline (Error bars are S.E.M.)

These inconsistencies are particularly problematic in amyloid imaging trials of new drugs, where the objective is to detect differences between a placebo group, where accumulation rates may be small (a few percent), and a drug group, where amyloid may either be removed (a decrease of a few percent) or slowed in accumulation. They are also problematic when evaluating subjects at the threshold of amyloid positive vs. negative, since this information is being used to help determine subject inclusion in clinical trials and to guide diagnosis in the clinic. The same problems influence measurements made of glucose, tau, or receptor binding activity, since the sources of variability are not imaging target dependent.

There are multiple technical factors that can contribute to the variability in measurement across reference regions. Currently accepted scanner quality control procedures typically allow a +/−10% variation from the mean of a uniform source (phantom) measured across the transaxial field of view of the scanner. This means that over time, the relative difference in measurement of the same radioactivity level at one physical location across the field of view as compared to another at a separate location could change by as much as 20%. Typically, scanners are maintained within a tighter range, but variability of a few percentage points is not uncommon. In clinical studies, changes of a few percent are often significant. Drift may also occur over time, as may the impact of or the correction method for signal scatter. Therefore, even without a change in the amyloid or other targeted entity to be measured using PET imaging, the ratio of a target ROI in one physical part of the brain (for example, toward middle or upper slices of the field of view) relative to that of a reference region located at a different transaxial location, particularly near the edge of the field of view, may change solely due to technical factors. This is added to any other tracer distribution phenomenon that may differ across the field of view that are not specifically due to the target binding entity itself.

There is a continuing need for improved scanning in imaging for human patients, such as using PET for brain scans.

SUMMARY OF THE INVENTION

A general object of the invention is to provide methods for evaluating the validity of a measurement of change in tracer signal between two longitudinal PET scans, obtaining measures of regional changes in tracer binding that are more accurate and reliable than those using conventional methods, and/or assessing the validity of a single scan measurement. Embodiments of this invention are particularly applicable to, and described herein with reference to, imaging of amyloid plaque in the brain, but have application with other radiotracers, and in SPECT, PET, or other imaging technology with other imaging agents.

The invention includes a method for correcting measurement variability across a scanner field of view within a scan from which an image is obtained or constructed, referred herein as an image scan. The method identifies and negates scan inconsistencies across the scanner field of view by normalizing values across the image scan as a function of reference signals measured across the field of view. The method operates preferably on a slice-by-slice method, but can compare groups of slices to other groups of slices, and/or function using adjacent slices.

In one embodiment, a second standard reference scan is used as a reference signal for the compensation of measurement variability across the field of view. The method includes determining a mean value for the field of view from the phantom scan, and adjusting measured signals during the image scan of patient tissue by multiplying each of the measured signals by an adjustment value of a scanning slice of the scan that includes the measured signal. The adjustment value is equal to an excursion of the measured signal from the phantom signal determined for the same scanning slice divided by the mean value for the field of view.

The invention further includes a method of calibrating or comparing two scans of a patient tissue by measuring and comparing imaging agent signals in each of a predetermined region of low imaging agent uptake and one or more predetermined regions of higher imaging agent uptake, across corresponding slices of the two scans. The signal can be reconciled for each of the region of low imaging agent uptake and the region of high imaging agent uptake between the slices by determining a transform value from a bias and slope of an equation that translates signals of a first of the two scans to signals of a second of the two scans, and applying the transform value to all slices of the second of the two scan. An extension of this approach is to use a non-linear equation that transforms the signals from three or more pre-determined regions from one scan to the second scan.

The method further includes comparing signal curves of the predetermined region of low imaging agent uptake and the predetermined region of high imaging agent uptake to determine a transform value from a bias and slope of an equation to reconcile the predetermined region of low imaging agent uptake and the predetermined region of high imaging agent uptake of each of the two scans to the other of the two scans. A percent deviation between resulting adjusted values between the two scans is calculated on a slice-by-slice basis, and determined to be within or not of a threshold value indicating that shape profiles of the two scans are adequately similar to reflect measurement of the same tissue.

The invention further includes calculating a percent change for each signal of two scans across the field of view, preparing a signal curve for the percent change across the field of view, and determining subject movement or scanner detection change from a deviation between the prepared signal curves. In another embodiment, a selected tissue region is measured through a plurality of slices and a validity of one or more measured signal of the tissue region is determined by comparing each measured signal across the plurality of slices to an acceptable range of values.

In one embodiment of this invention, the method includes providing a plurality of image slices of a tissue, measuring an imaging agent, such as a PET imaging tracer, in a region of interest within each of the plurality of slices, measuring the imaging agent in a reference region within each of the plurality of slices or an adjacent slice, and normalizing the plurality of slices as a function of measured imaging agent differences across reference regions of the plurality of slices.

In one embodiment, the method profiles the trajectories of tracer signal throughout the brain, slice-by-slice—raw signal and percent change in raw signal—between scans by measuring the signal intensity in a mask (boundary) representing the region of interest, slice-by-slice. The method can be used to image regions including: transaxial, coronal, or sagittal slices; reference tissue: gray, white, eroded/retracted white, CSF, eroded/retracted CSF; other reference regions: cerebellar gray, whole cerebellum, pons and/or brainstem; and/or volumes of interest (VOI), which may include, without limitation, anterior cingulate, frontal cortex, posterior cortex, precuneus, inferior parietal cortex, lateral temporal cortex, medial temporal region, striatum, occipital cortex, and/or thalamus. Embodiments of this invention can be performed with or without correction for partial volume effects (PVE correction), and the method can measure as an average value for that slice, measure as a standard deviation, and/or measure as a difference from the mean across slices.

In one embodiment, the method compares the percent change in a proposed reference region (such as gray cerebellum, whole cerebellum, or pons) to that in an amyloid resistant set of tissue located in the same slices as the target VOI to be measured, to determine whether the reference region will be a valid basis for comparison.

In one embodiment, the method constructs an amyloid resistant reference volume, which may vary across the transaxial, coronal, and/or sagittal distance of the brain, such as: by selecting tissue in structures known from the literature (e.g., Edison P et al., Neurology, 2007; Ziolko S et al., *NeuroImage*, 2006; Huang K-L et al, PLoSONE, 2013) to accumulate amyloid more slowly than other regions, such as sensorimotor cortex, thalamus, medial temporal regions, cerebellum, portions of occipital cortex, portions of precentral gyrus; by gray masking the baseline PET image, and thresholding to the top x % (e.g., 55%) of voxels in the PET image, and removing those voxels from the gray masked PET image, in which the resulting mask which will then serve as an amyloid resistant reference; by interpolation between slices and "smoothing" of the amyloid resistant profile across slices by thresholding a PET scan from the subject without use of the MRI for masking; and combinations thereof. These embodiments may or may not be performed with or without partial volume effects correction of the baseline scan prior to thresholding. The same approach may also be taken for tracers targeting tau or other entities, in the case of tau identifying those regions that resistant to tau accumulation in the subject population of interest.

In embodiments of this invention, the method includes a design (definition) of an amyloid resistant mask or reference region within the brain. The method can include the use of the following tissue volumes as reference regions, without a slice-by-slice approach: an amyloid resistant mask; a full gray matter mask; a full white matter mask; and/or a combined gray, white, and/or CSF mask.

The invention includes methods for measuring changes of other tissue signal in the brain, referenced to the reference region (intensity normalized). The methods can be performed by taking a ratio of the value of the VOI within a particular brain slice to the value of the reference tissue within that same slice or a set of nearby slices; by regression; by co-varying; by other reference methods; or by voxel-, slice- and/or average-based methods.

The invention includes a method for evaluating the stability of a single scan by comparison of pons, cerebellum (gray, whole), white, gray, CSF at baseline or static scan to assess validity, and comparison of the white, gray, CSF.

Embodiments of this invention include methods for correcting for contribution of white spillover to gray, such as, through a calculation, through PVE correction and/or through comparison of gray segment masked vs. unmasked VOIs.

The method of this invention can be applied to, for example, amyloid PET tracers, FDG PET, Tau or tangle tracers, dopamine transporter tracers, monoamine related tracers, SPECT imaging tracers, and other tracers.

The method of this invention may be performed through manual or semi-automated calculation, but is desirably implemented automatically via software stored on a recordable medium, and executed by a data processor, such as a computer in connection with conventional or modified imaging equipment.

Other objects and advantages will be apparent to those skilled in the art from the following detailed description taken in conjunction with the appended claims and drawings.

DETAILED DESCRIPTION OF THE INVENTION

Figure 1:
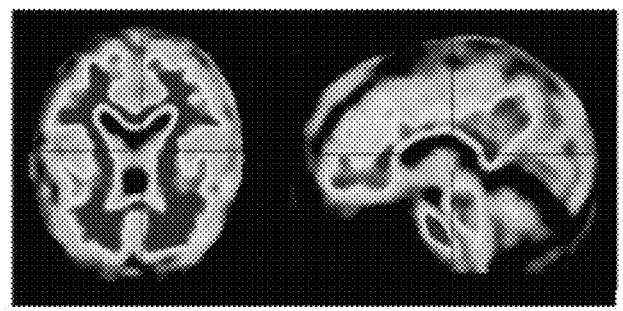
FIG. 1 shows a sample amyloid PET scan in transaxial and sagittal views.
Figure 2:
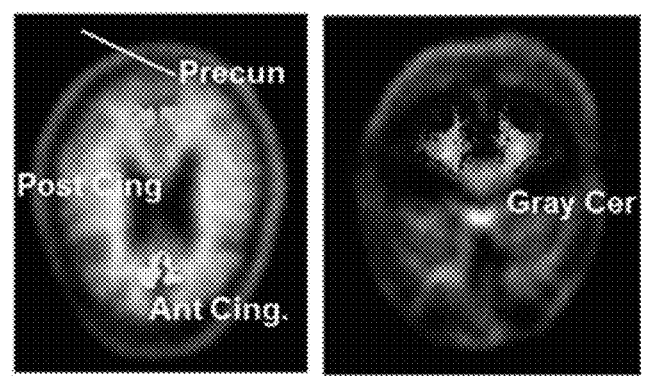
FIG. 2 shows sample VOIs and a sample reference region (Gray Cerebellum) overlaid on an amyloid PET image.

The invention provides methods, implemented desirably automatically through computer readable coded instructions, for correcting measurement variability within an image across an image scanner field of view. Data discrepancies between scans can occur for various reasons, such as detector misalignment across a scan field of view and/or scanning differences between two scans, such as by different scanners, imaging agent dose, injection delay, subject weight, or subject position, motion, scatter correction, scanner sensitivity, etc. The invention addresses the issues associated with measurement inconsistency and noise, thereby allowing for more accurate imaging and comparison between multiple scans for a patient.

The method and apparatus and/or software of this invention correct for measurement variability across a scanner field of view within an image scan. The method, implemented through an imaging system, identifies and negates scan inconsistencies across the scanner field of view. In embodiments of the invention, this is accomplished by normalizing values across the image scan as a function of reference signals measured across the field of view. As an example, by aligning reference and target regions in transaxial locations, the method reduces or eliminates acquisition-related variability, benefiting measurement accuracy and statistical power.

In one embodiment of this invention, the reference signals are obtained from a separate phantom scan of a uniform radiation or measured signal source across the scanner field of view. A mean value is determined for the field of view from a scanning of the phantom object, such as are known and available. Measured signals for a tissue scan are adjusted, slice by slice, by multiplying each of the measured signals by an adjustment value of the scanning slice that includes the measured signal. The adjustment value is equal to an excursion (residual, percent of mean value for the cylinder) of the measured signal from the phantom signal that was determined for the same scanning slice, divided by the mean value for the field of view. The result is identical measures for each slice across the scanner field of view for the same source radioactivity value within the scanner. In one embodiment of this invention, the phantom source used to measure scanner variability has one or multiple levels of radioactive source distributed uniformly across the entire field of view of the scanner, so that detection of multiple signal levels on a slice-by-slice basis may be measured.

The reference signals can alternatively be obtained within the image scan itself, such as from one or more reference regions of a patient tissue within the image scan. In many embodiments of this invention, the reference region or reference volume refers to a region or volume, respectively, of a tissue, such as an organ, known or determined to have a comparatively low signal, or be "poor", for the imaging agent, such as a region known not to accumulate the imaging agent and/or a region having non-specific binding for the imaging agent. The resistant tissues can obtain little or no imaging agent, or can include some imaging agent but be a non-specific binding region for the imaging agent. As one example, the reference region for a brain scan can be white matter brain tissue. Brain white matter is both high uptake for PET amyloid imaging tracers and amyloid poor. Amyloid itself does not accumulate in white matter. However, the amyloid tracers (or at least several of them) bind within white matter due to, for example, non-specific binding to other substances in the white matter and also a lower clearance rate from the brain. White matter has become a reference region of choice for some researchers because it has high signal (non-specific, but quite consistent from scan to scan) and is present throughout much of the brain.

In one embodiment of this invention, the method corrects for variability across the scanner field of view, using two types of reference regions, such as both one or more low signal reference regions and one or more high signal reference regions, within a scan. This method is useful for calibrating or comparing two scans of a patient tissue by measuring and comparing imaging agent signals in each of a predetermined region of low imaging agent uptake and one or more predetermined regions of higher imaging agent uptake across corresponding slices of the two scans. A second scan, such as taken of the patient at a second date, can be calibrated to an earlier first PET scan by measuring the values in a defined region of lower tracer uptake (for example, cerebrospinal fluid (CSF) or gray tissue known to be devoid of tracer binding) at each slice across the scanner field of view; measuring the values in a defined region of higher tracer uptake (for example, white matter) at each slice across the scanner field of view; reconciling the lower and higher uptake signal profiles of the first and second scans to each other by determining at each slice the bias (intercept) and slope (sensitivity) of the equation that translates the second set of corresponding low and high values to the first set of low and high values; and applying the calculated transform to all regional measurements of the second scan on a slice by slice basis.

In some embodiments, it is desirable to use a lowest x % of the values of the low threshold region. For example, to eliminate metabolite or other induced "halo" effects, the low value signal (for example, CSF if the organ is the brain and cerebrospinal fluid) is calculated as the average of the voxels within a region excluding the highest x %, or including only the lowest y %, in order to eliminate the possible influence of higher signal intensities.

In one embodiment of this invention, the method detects whether the comparison between two longitudinal scans of the same subject is valid, such as in the absence of slice-by-slice calibration between scans. The method compares a second PET scan to a first PET scan, whereby the signal in one or more regions is measured on a slice-by-slice basis and a signal profile is created over the scanner field of view for each scan. The curves are compared for the ability to use a single transformation (bias, slope) to reconcile the low signal and high signal measurements of the two scans to one another. The percent deviation between resulting (adjusted) values are calculated on a slice-by-slice basis, and determined to be within or not of a threshold value indicating that the shape profiles of the scans are adequately similar to reflect measurement of the same tissue.

Figure 7A:
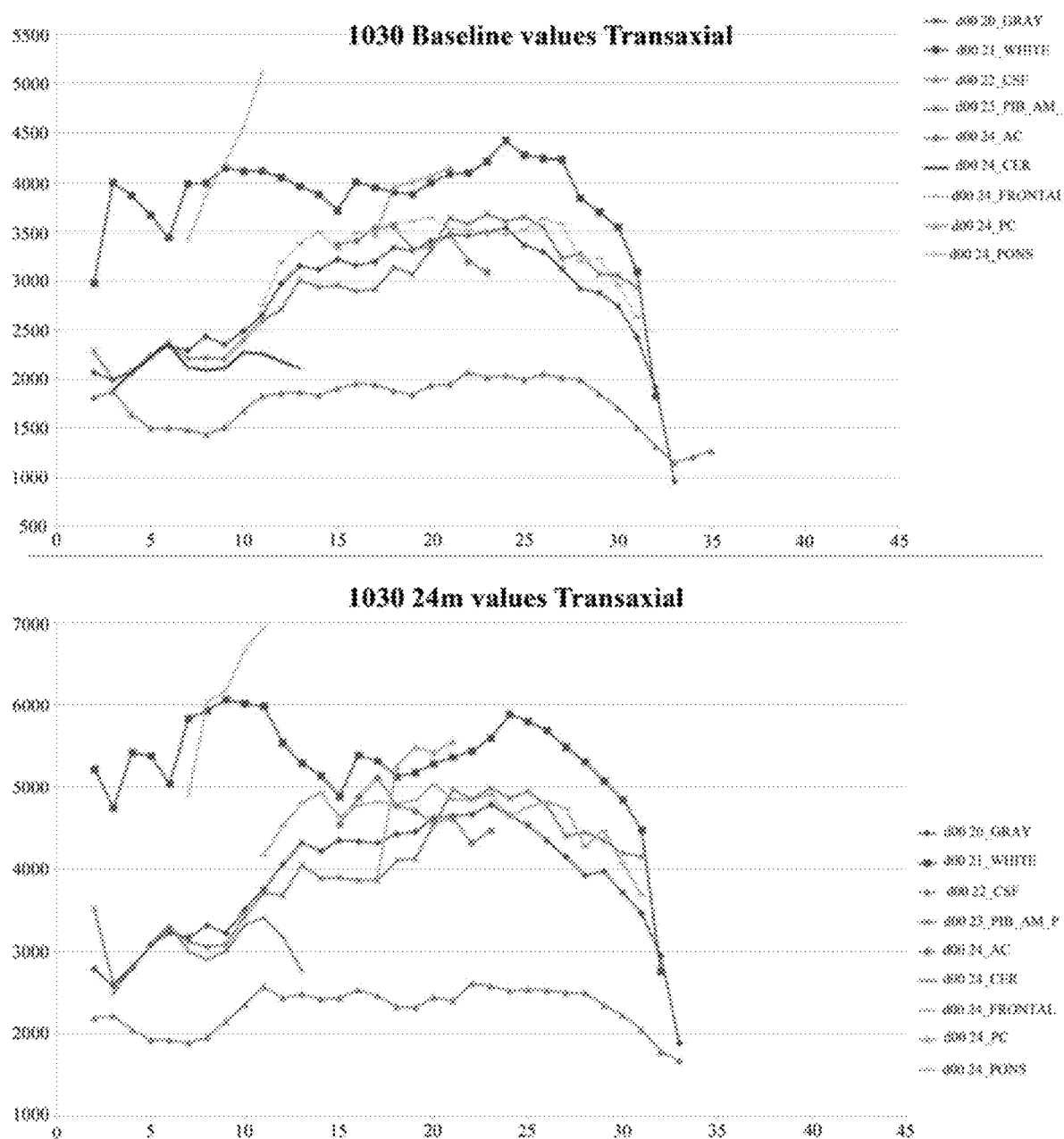
FIG. 7A shows two representative scan signal curves of a tissue for illustration purposes.
Figure 7B:
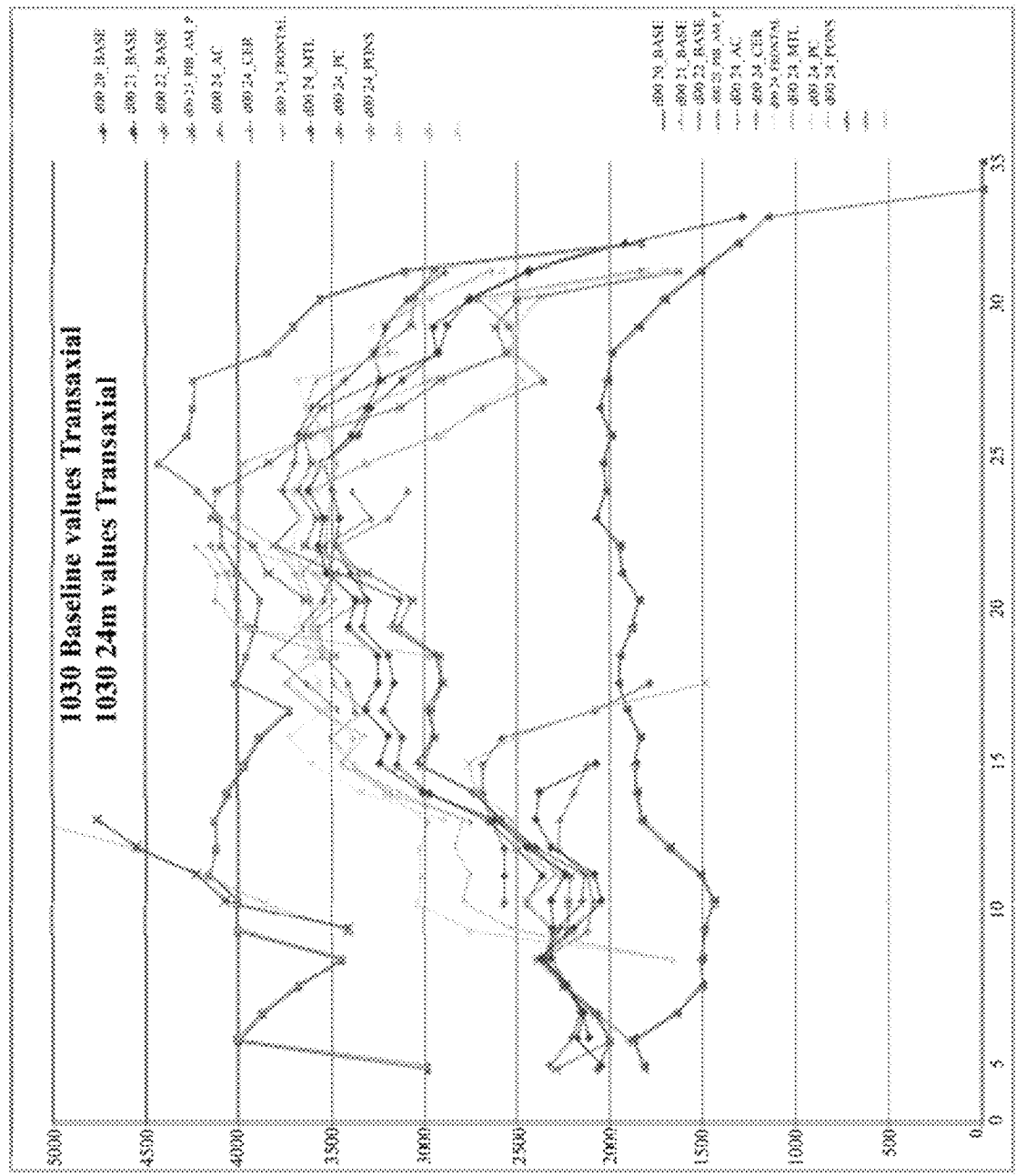
FIG. 7B shows a resulting scan curve of the mathematically combined scans of FIG. 7A.

FIGS. 7A-7B illustrate an embodiment of reconciling signals for each of the predetermined region of low imaging agent uptake and the predetermined region of high imaging agent uptake between the slices. FIG. 7A shows two scans. FIG. 7B illustrates a representative resulting overlap of the two scans of FIG. 7A. The overlap results from comparing signal curves of the region of low imaging agent uptake and the region of high imaging agent uptake. The transform value is determined from a bias and slope of the equation that reconciles the region of low imaging agent uptake and the region of high imaging agent uptake of each of the two scans to the other of the two scans. A percent deviation between resulting adjusted values between the two scans is calculated on a slice-by-slice basis, and determined to be within or not of a threshold value indicating that shape profiles of the two scans are adequately similar to reflect measurement of the same tissue.

As will be appreciated by those skilled in the art, scan quality control and acceptance measures will generally be performed as needed prior to the method of this invention. This may be particularly true for comparisons of two different scans, where the patient position, etc. may be different between scans. Known and available methods for coordinating two scans can be implemented prior to or during methods of this invention. As such the slice-by-slice comparison in particular embodiments of this invention refer to adjusted and coordinated tissue slices from the scan, which may not be the exact same as the original detector scanning slices taken by the imaging device.

One embodiment of this invention includes a method to detect whether a scanner profile change has occurred that may invalidate the image measurement. A percent change between the non-normalized signal in a first scan and a second scan is calculated, and the value at each slice determined across the scanner field of view. The profile (approximately linear with a plateau in the middle, vs. wave like, vs. an increasing or decreasing slope over the field of view of the scanner) is determined and compared across one or more regions of interest. A deviation from a linear, plateaued % difference profile will indicate either subject motion or a significant change in scanner detection characteristics across its field of view. In one embodiment, the value within a selected tissue region is measured on a slice-by-slice basis and a validity of the profile of signal change from slice to slice is determined to be stable or not based upon its slope or fit to an acceptable range of values.

The invention also includes measurement of relative tissue values, such as where the reference region to which a target region of interest is compared (through numeric comparison of the magnitude of measured signal or else the ratio of the target region to reference region or vice versa) is based upon the measurement of white matter vs. the region of interest in the slice of interest, or in multiple slices in proximity to the designated slice. The reference region comparison can be made between the target tissue and the white matter tissue in proximity to the target tissue within the slice or proximal slices, such as an adjacent or abutting slice (i.e., not the whole slice, but a subset of the tissue in proximity to the target).

The invention includes a method of measuring relative signal intensities in tissue, such as within the brain, by quantifying the signal in one or more volumes of interest and reference volumes in each of a set of slices traversing the brain, and comparing changes specific to their slice location to assess stability of reference regions and relative change, and then, when necessary, normalizing the plurality of slices as a function of differences across reference regions of the plurality of slices. This differs from conventional methods that assume consistency across the brain and use an average of one or more regions such as cerebellum, pons, white matter, taken as a whole, and then divide or regress the means of other tissue volumes in other locations of the brain against the values of those reference volumes.

In one embodiment of the invention, an imaging agent is measured in a region of interest within each of the plurality of slices. The region of interest is generally a portion of a tissue volume of interest that correspondingly occurs in each measured slice. The imaging agent is also measured in a reference region within each of the plurality of slices or an adjacent or directly abutting slice if needed (such as if the slice is lacking any or sufficient reference tissue). Each of the plurality of slices is normalized as a function of measured imaging agent differences across reference regions of the plurality of slices.

The normalizing can be accomplished using a determined ratio of the measured imaging agent between the region of interest and the reference region for each of the plurality of slices. In one embodiment, trajectories and/or percent changes between regions of interest and/or reference regions are compared as they traverse at least two of the plurality of slices. Desirably, the scan is normalized to a consistent reference region imaging agent count across the plurality of slices, such as, without limitation, normalizing each of the plurality of slices, or groups of slices, to a consistent ratio of the measured imaging agent between the region of interest and the reference region.

As a representative example of one embodiment of this invention, two longitudinal scans are obtained from the same subject. One region in the subject's brain remains stable with regard to amyloid burden for those two scans; as an example, let the value of this region be 12,000 counts of measured radioactivity in the first scan. A second, reference region in the subject also remains stable with regard to amyloid burden for those two scans; as an example, let the value of this region be 10,000 counts of measured radioactivity in the first scan, making the SUVR 1.2. If neither region is changing, then a SUVR of 1.2 is expected in the second scan. This is possible if neither count value changes (so 12,000 and 10,000). This is also possible if both regions change by the same percentage (multiplicative, not by an additive bias), as follows: for example, let's say it is a 20% change, then the VOI becomes 12,000*(1+20%)=14,400, and the reference region becomes 10,000*(1+20%)=12,000, and the SUVR is 1.2 again.

However, if the two regions change by different percentages, or by an additive bias, the SUVR will not remain stable. For example, if the VOI changes by 20%, to 14,400, but the reference region changes by 10%, to 11,000, the new SUVR is 1.309, and it appears that our amyloid burden increased by 8% between the scans. Alternatively, if both regions change by an additive bias, for example +3000 counts, the SUVR becomes 15,000/13,000=1.15, and it appears that the SUVR decreased by 4%.

Therefore, valid signal comparison requires that stable regions either result in the same number of absolute counts or that they (i.e., the target VOI and the reference region) change by the same percentage. It follows that if the raw signal in a presumably stable region is changing by one percentage, but that the raw reference region signal changes by another percentage, then the measurement for those and any other regions will be unstable. Further, the brain is no longer presumed to be static from one end to the other, but rather that signal may vary from slice to slice, not due to the target (such as amyloid) of interest, but due to other factors such as scanner detection profile, software, or tracer clearance.

Figure 8:
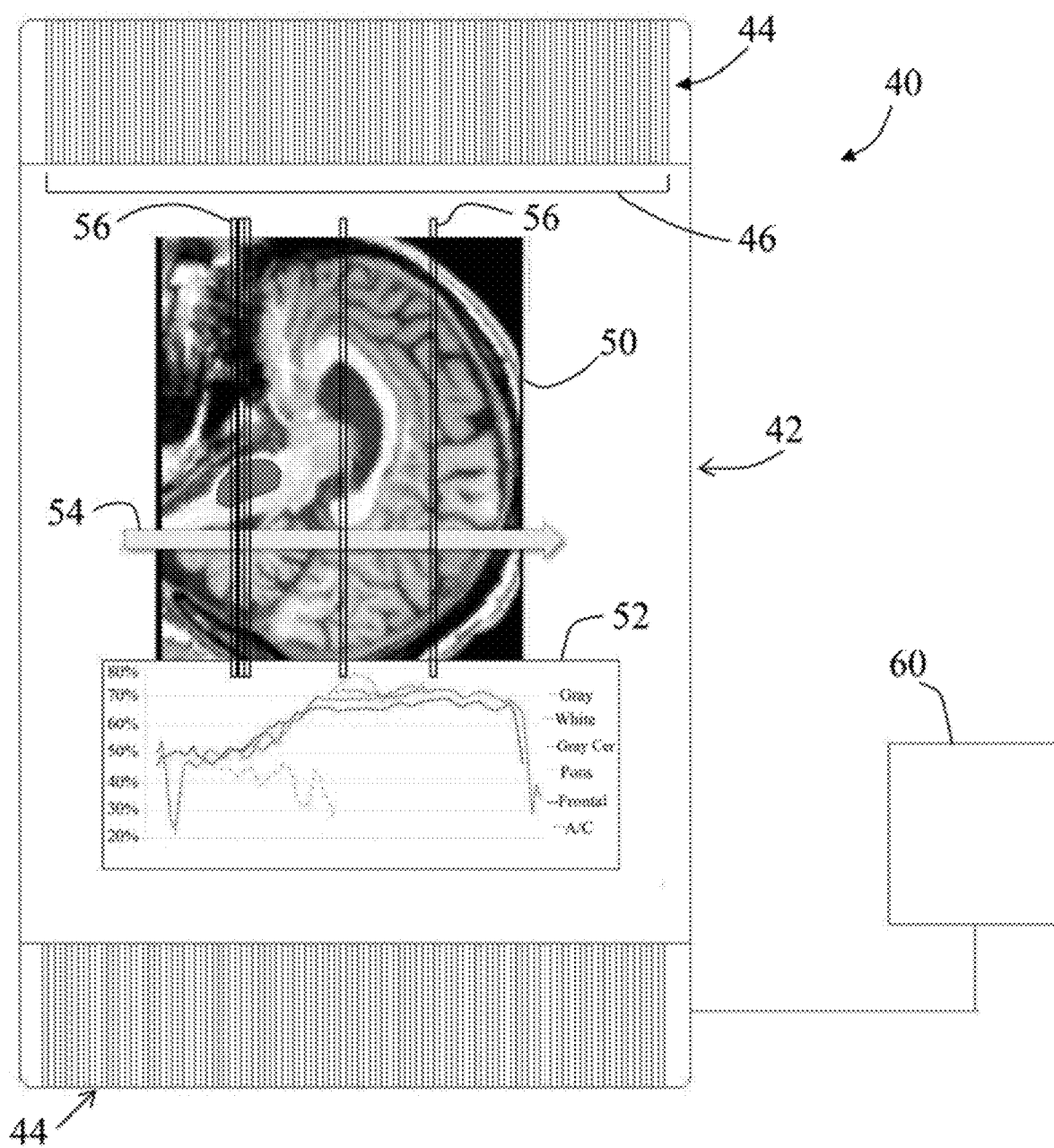
FIG. 8 representatively illustrates use of an imaging device, according to one embodiment of this invention.

FIG. 8 representatively illustrates a scanning imaging device and a brain scan according to one embodiment of this invention. The scanner 40 includes a patient compartment 42. Surrounding the patient compartment is a plurality of detectors 44 extending across and creating a field of view 46. The patient is represented by an illustrated brain image 50, along with an exemplary scan signal curve 52 for the brain image 50. Arrow 54 shows a scanning direction and across the image are illustrated a few representation slices 56.

A computing system 60 is representatively shown in controlling combination with the scanner device 40, and includes a data processor, recordable medium, and operating software code. The computing system can include coded instructions for scanning the tissue, and for analyzing the scanning signals. The system 60, or any add-on memory device, can also include software coded instructions for automatically executing each step of the methods of this invention. The coded instructions can be integrated into the system operating code, be an add-on module, or be implemented in a stand-alone computer system.

Referring to the slices in FIG. 8, to assess the stability of various reference regions according one embodiment of this invention, as well as the stability or profile of the PET signal across the brain, the signal for each volume of interest (VOI) is measured in each transaxial slice 56 as the imaging travels upward through the brain (arrow 54). Each slice 56 provides a data point for a particular VOI, so that the profile of the VOI can be seen as the scanner field of view is traversed.

For example, while a typical VOI measure might yield:

| VOI | Mean | S.D. | Min | Max | No. of voxels |
|---|---|---|---|---|---|
| Anterior Cingulate | 35 | 3 | 2 | 47 | 400 | the slice-by-slice version of one embodiment of this invention would yield this information plus:

| VOI | VOI Slice | Brain slice | Mean | S.D. | Min | Max | No. of voxels |
|---|---|---|---|---|---|---|---|
| Anterior Cingulate | 1 | 38 | 30 | 3 | 2 | 40 | 35 |
| Anterior Cingulate | 2 | 39 | 34 | 4 | 20 | | 40 |
| Anterior Cingulate | 3 | 40 | 35 | 3 | 26 | | 50 |
| Anterior Cingulate | 4 | 41 | 37 | 5 | 28 | | 45 |
| Anterior Cingulate | ... | ... | ... | ... | ... | | ... |
| Anterior Cingulate | 14 | 51 | 27 | 5 | 7 | | 20 |

The scanning or tissue slices of this invention may be transaxial slices, coronal slices, or sagittal slices, or all or other directional scan, or in quadrants or sections, depending upon the VOI. However, a presently preferred implementation is in transaxial slices as shown in FIG. 8.

As one important aspect of measurement, the amyloid "poor" gray is measured as representative of the "carrier signal" throughout the brain, and as possibly the best reference region for SUVR calculation. Amyloid poor gray is defined as that portion of the brain that is not prone to accumulating amyloid, and thus a better term for it may be "amyloid non-vulnerable" or "amyloid resistant." Amyloid negative subjects or subjects who are in the process of accumulating amyloid may have significantly more brain tissue that is negative for amyloid but not a valid "amyloid poor" reference because it may well accumulate amyloid over time. The amyloid resistant mask (or VOI) can be constructed as follows: (a) using an a priori (fixed) set of regions that have been shown in the literature (Edison et al., 2007; Ziolki et al., 2006; Huang K-L et al., 2013) not to be as vulnerable to amyloid accumulation; and (b) by thresholding the subject's baseline PET scan, masked with gray segment MRI if available, to find those regions that are amyloid "rich", and then removing those from the mask that is applied as the amyloid resistant mask.

Figure 9:
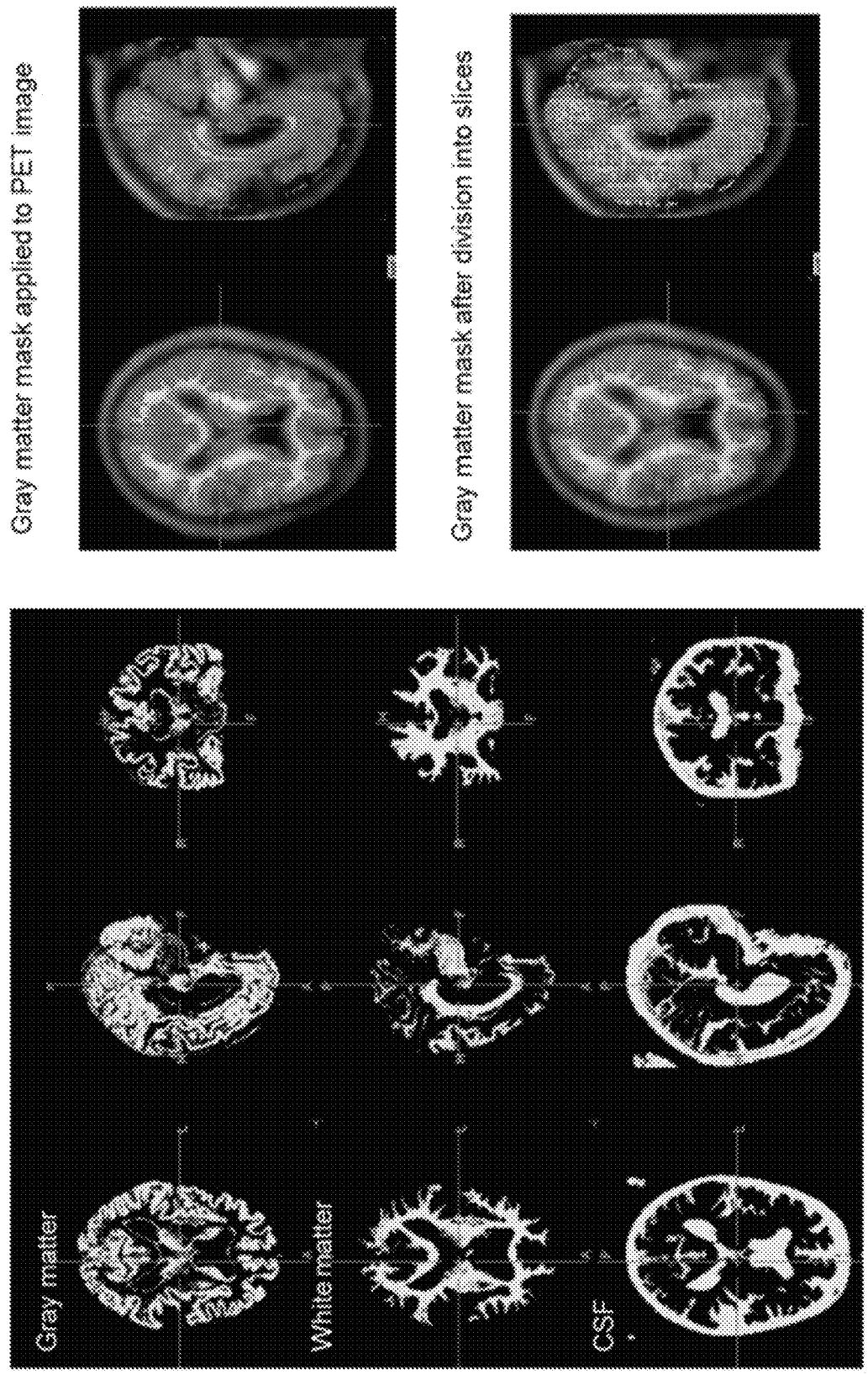
FIG. 9 shows an example of gray, white, and CSF MRI segments, and the application of a slice-by-slice gray segment to a PET scan.

For reference, FIG. 9 shows an example of gray, white, and CSF MRI segments, and the application of a slice-by-slice gray segment to a PET scan. If an individual subject MRI is not available, these can be probabilistic, i.e., based upon a template.

To assess reference region validity, the % change in candidate reference regions is compared to the % change in amyloid resistant, white, and CSF reference regions, throughout the slice-by-slice profile of the brain. A difference between the percent change in the candidate reference region and that in stable tissue that should be changing in its raw value by the same percentage indicates that there is a validity issue and that the candidate reference region may under- or over-estimate change in other tissue.

It is important to note that all scans may not be "flat" in profile and therefore a different reference (i.e., the slices in that particular set of slices) may be most relevant and accurate depending upon where it is located in the brain.

In addition, a retracted white matter mask (that is, retracted from gray tissue boundaries) can be applied to assess whether changes in the white matter profile are due to spillover of amyloid signal from gray matter or alternatively, due to other scanner detection phenomenon or tracer clearance changes that do not relate to amyloid but affect measurements. Further, a partial volume effects correction can be used to further determine whether changes in profiles are due to spillover or alternatively due to scanner detection changes. Finally, changes in VOIs such as anterior cingulate, posterior cingulate, frontal cortex, precuneus, lateral temporal cortex, lateral parietal cortex, etc. are evaluated as compared to the profile of the amyloid resistant gray region. Testing was made as similar as possible to the exposure that the gray tissue has in both cases to surrounding CSF and white tissue, given that spill-in from those different tissues to gray matter will occur, as well as the converse.

The present invention is described in further detail in connection with the following examples which illustrate or simulate various aspects involved in the practice of the invention. It is to be understood that all changes that come within the spirit of the invention are desired to be protected and thus the invention is not to be construed as limited by these examples.

EXAMPLES

The examples below use subjects from the Alzheimer's Disease Neuroimaging Initiative (ADNI) database.

Application Example 1

ADNI Subject

The subject was imaged at three visits with 11C-PiB, and changed trajectory with regard to cortical average as referenced to gray cerebellum and pons, both times in magnitude well beyond average. However, when referenced to subcortical white matter, changes were minimal. The ADNI reported values are shown below. A Biograph HiRez scanner was used on all three occasions.

|  |  |  | Cortical Average SUVR, referenced to: | | | Percent change from prior scan, ref. to: | | |
|---|---|---|---|---|---|---|---|---|
| Subject | Visit | Dx at time of scan | Gray cer | Pons | Subcort WM | Gray cer | Pons | Subcort WM |
| 566 | m12 | MCI | 2.126 | 1.155 | 1.181 |  |  |  |
| 566 | m24 | MCI | 2.368 | 1.369 | 1.155 | 11% | 18% | −2% |
| 566 | m36 | AD | 2.070 | 1.232 | 1.190 | −13% | −10% | 3% |

Figure 10:
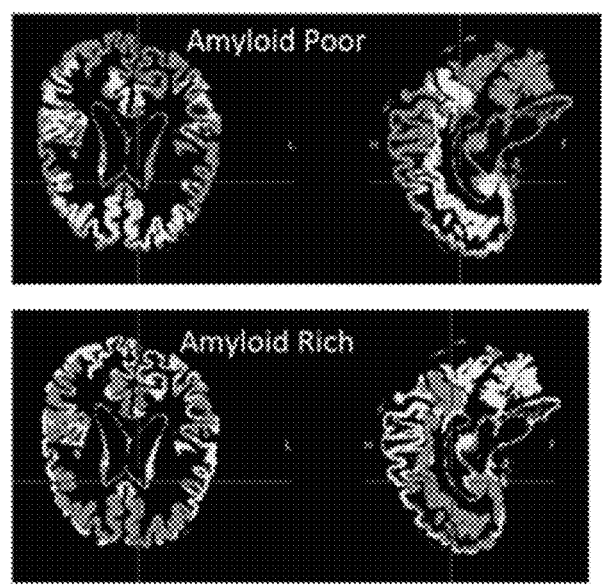
FIG. 10 shows examples of an Amyloid Poor (amyloid resistant) mask and an Amyloid Rich mask.
Figure 4:
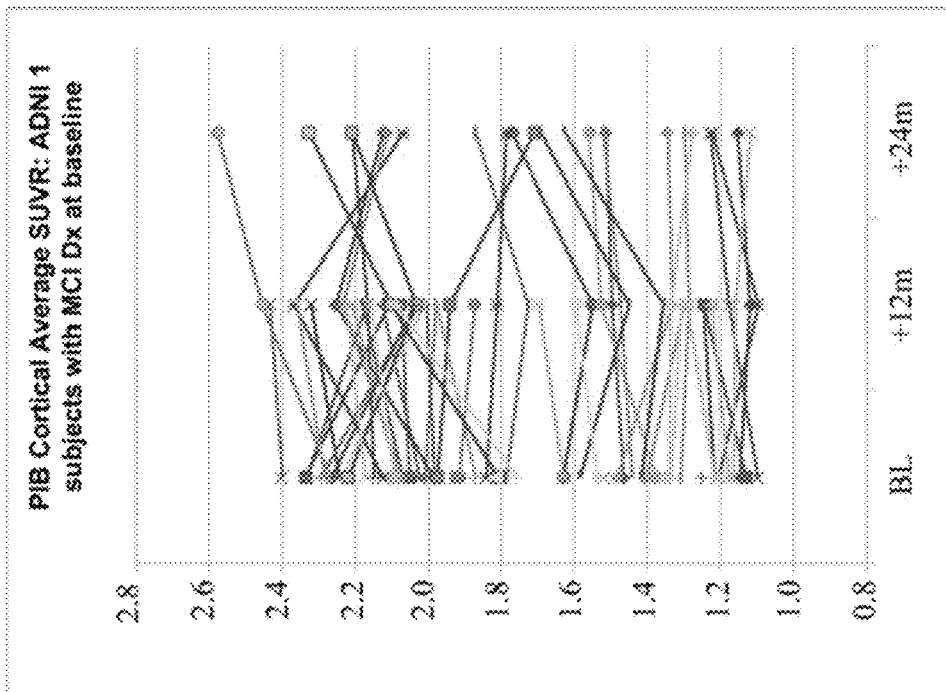
FIG. 4 shows the longitudinal trajectories of the "amyloid burden," or cortical average SUVRs of subjects with Mild Cognitive Impairment (MCI, often a precursor clinical state to AD dementia) imaged using 11C-PiB, with values posted by ADNI.
Figure 3:
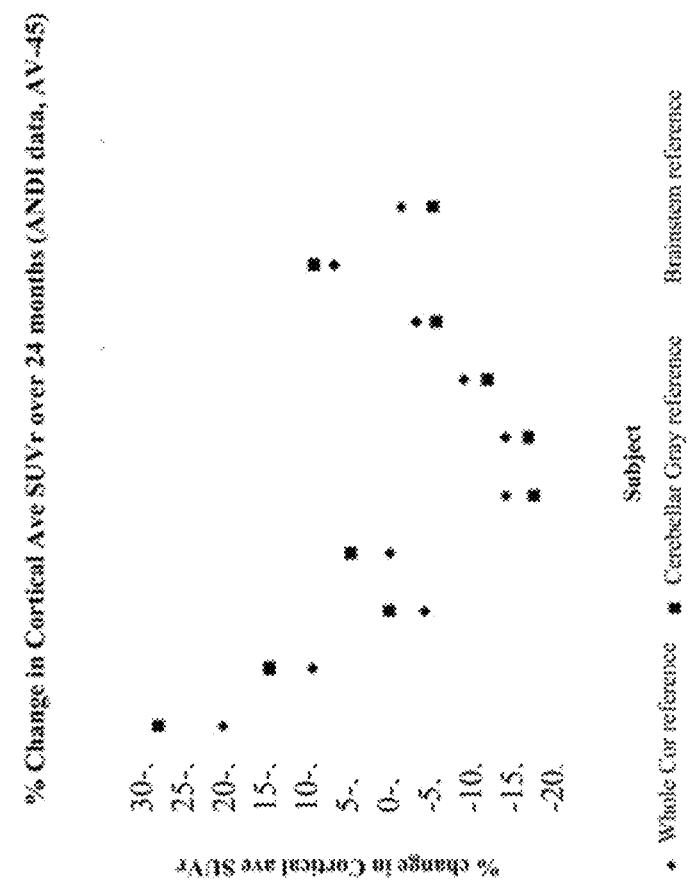
FIG. 3 is shown a plot of the percentage change in cortical average SUVR using whole cerebellum, gray cerebellum, and brainstem reference for ten example subjects, between two scans, 24 months apart.
Figure 5:
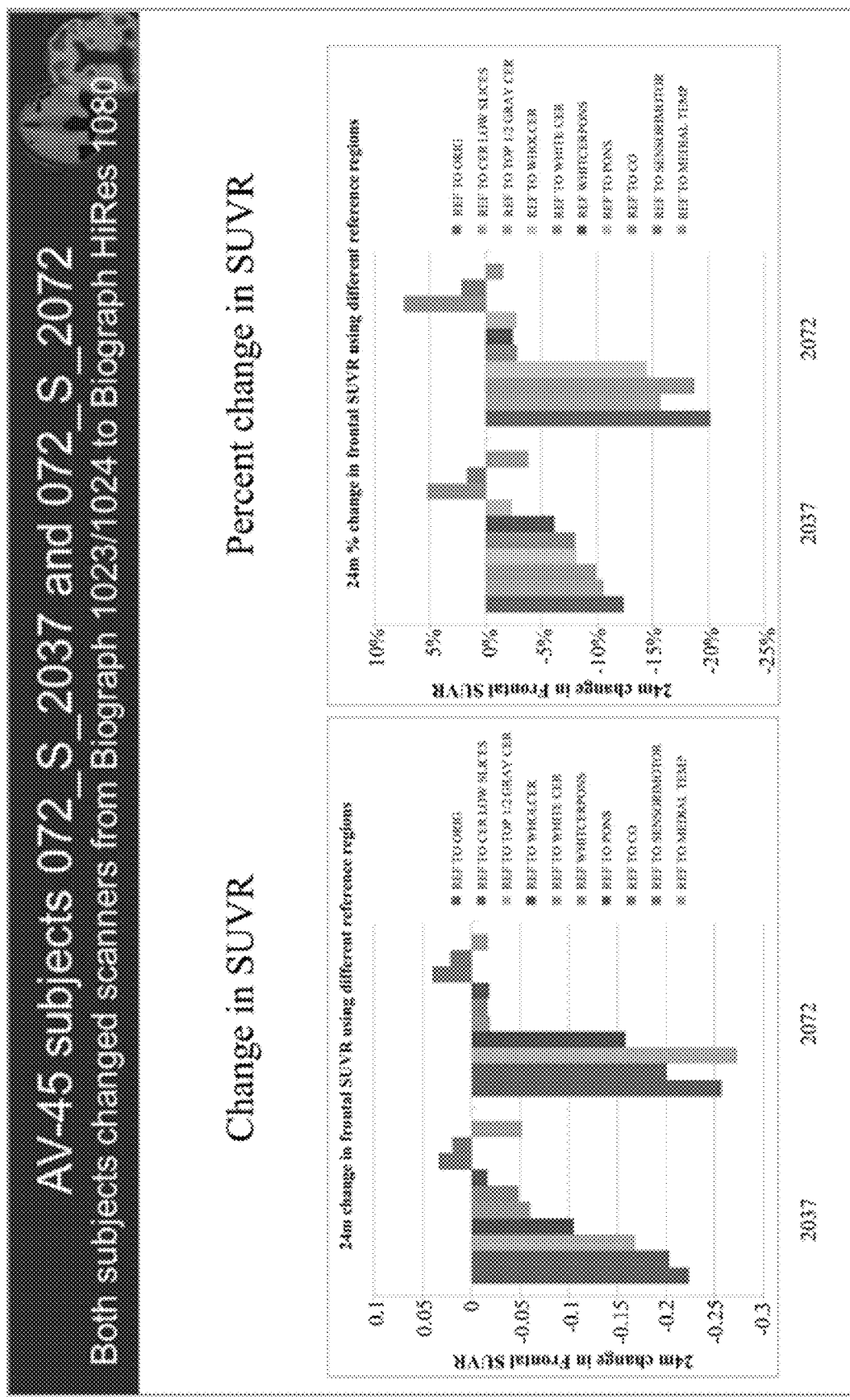
FIG. 5 shows differences in the absolute and percent change in longitudinal SUVR for two different subjects who were each measured on one scanner model at baseline and a different scanner model 24 months later.
Figure 6:
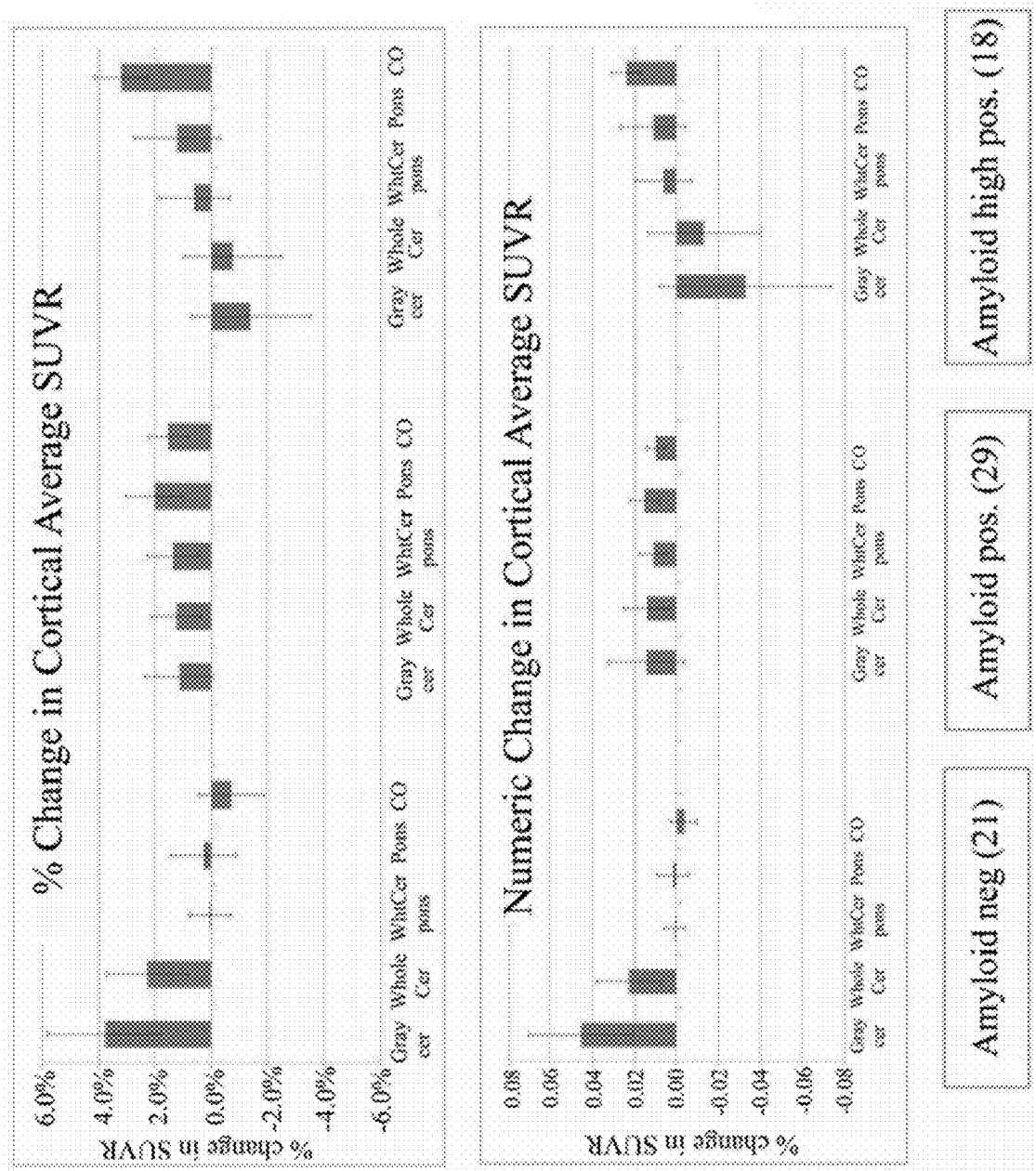
FIG. 6 shows longitudinal trajectories in subjects imaged at 24 month intervals.

FIG. 10 shows examples of an amyloid poor (amyloid resistant) mask and an amyloid rich mask, with amyloid shown by dark gray. It is noted that these masks can and would be further refined by removing the tissue outlining the pons and brainstem, and just adjacent to CSF in the frontal region.

Figure 11:
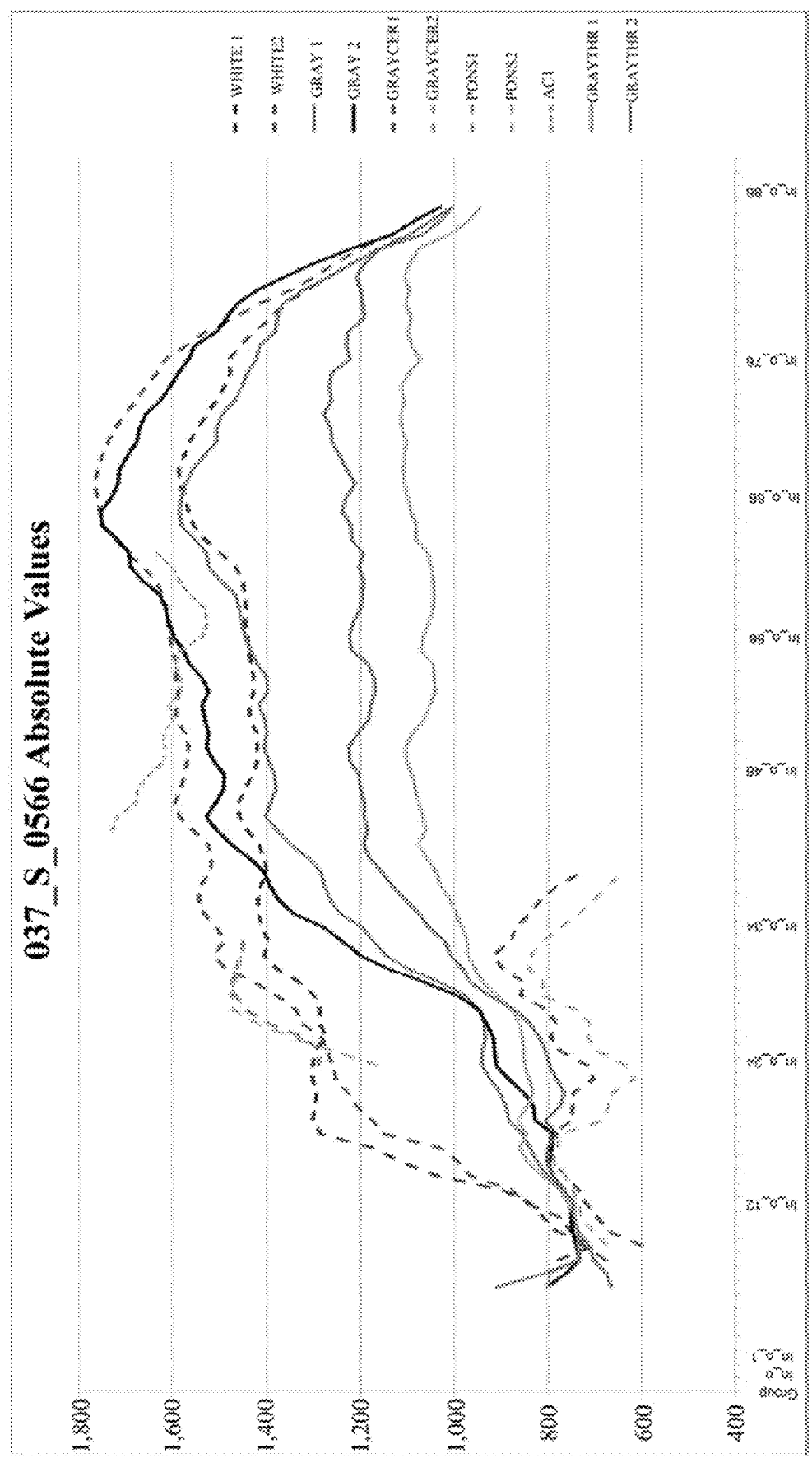
FIG. 11 shows raw, non-intensity normalized values for selected reference regions for two longitudinal scans for an example subject.

FIG. 11 shows the raw, non-intensity normalized values for each slice for several regions of interest and references. For example, gray matter was measured using the gray segment mask produced through the SPM (Statistical Parametric Mapping, the Welcome Trust) segmentation procedure from the subject's MRI scan. White matter was measured using the white segment mask produced through the same segmentation, as is CSF (cerebrospinal fluid). The anterior cingulate (AC) was measured by assigning a volume of interest (boundary) over several slices upon that structure of the brain as defined using the subject's MRI scan, and then gray matter masking (thresholding) the VOI to include only gray matter. The two lower solid lines, which are amyloid resistant or poor regions, are lower in intensity than the upper two solid lines, which are gray matter as a whole. The dotted anterior cingulate (AC) scan 1 line is higher than the Gray 1 line, consistent with the amyloid rich nature of the AC. The cerebellum (lowest dotted lines for Scan 1 and Scan 2) comprise much of gray matter in the lower slices, but are lower than gray matter as it traverses through the brain, as well as amyloid resistant gray matter, due to being amyloid devoid, but possibly also due to other transaxial location factors as well.

Figure 12:
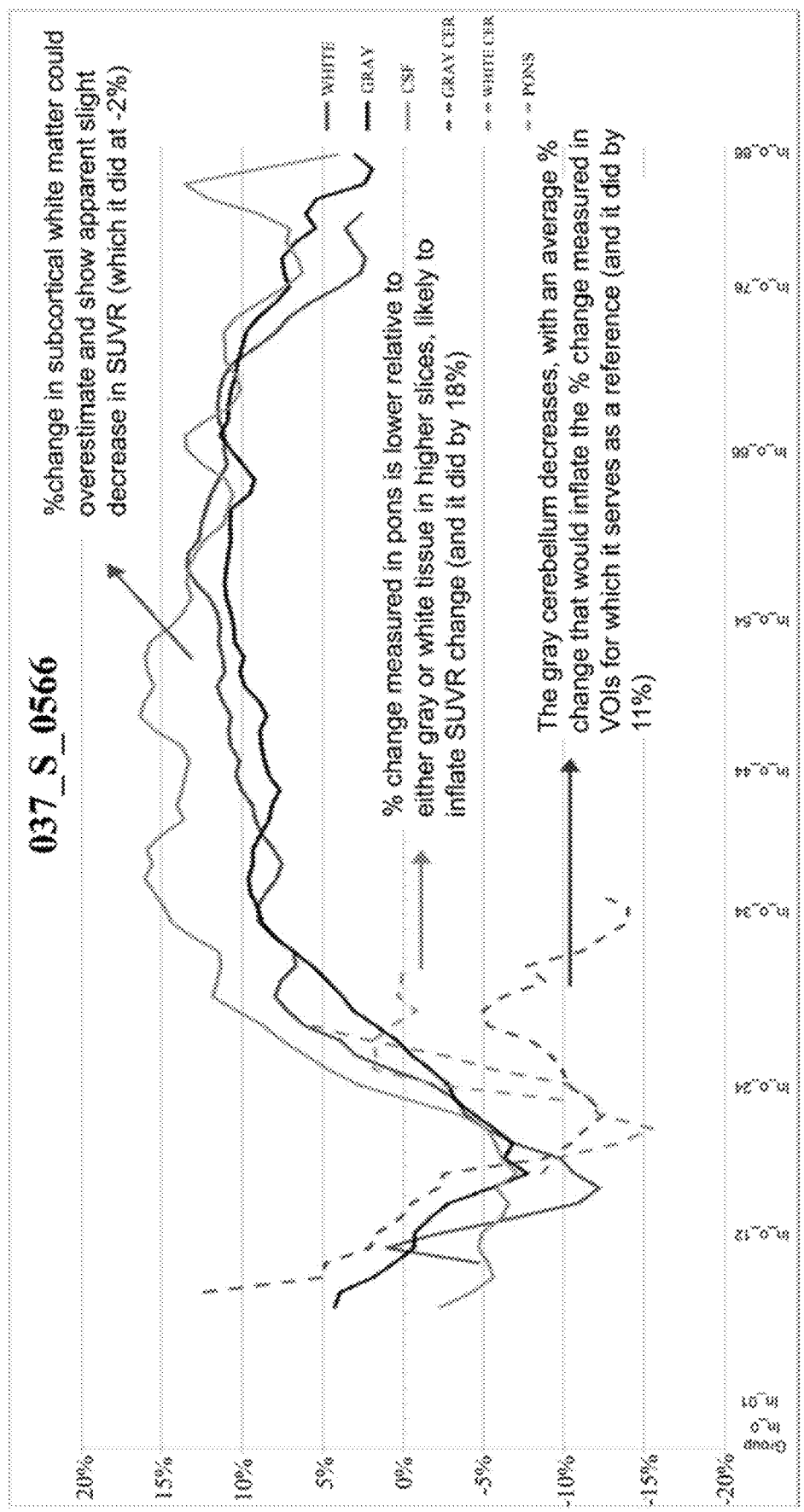
FIG. 12 shows percent change in selected reference regions the example subject.
Figure 13:
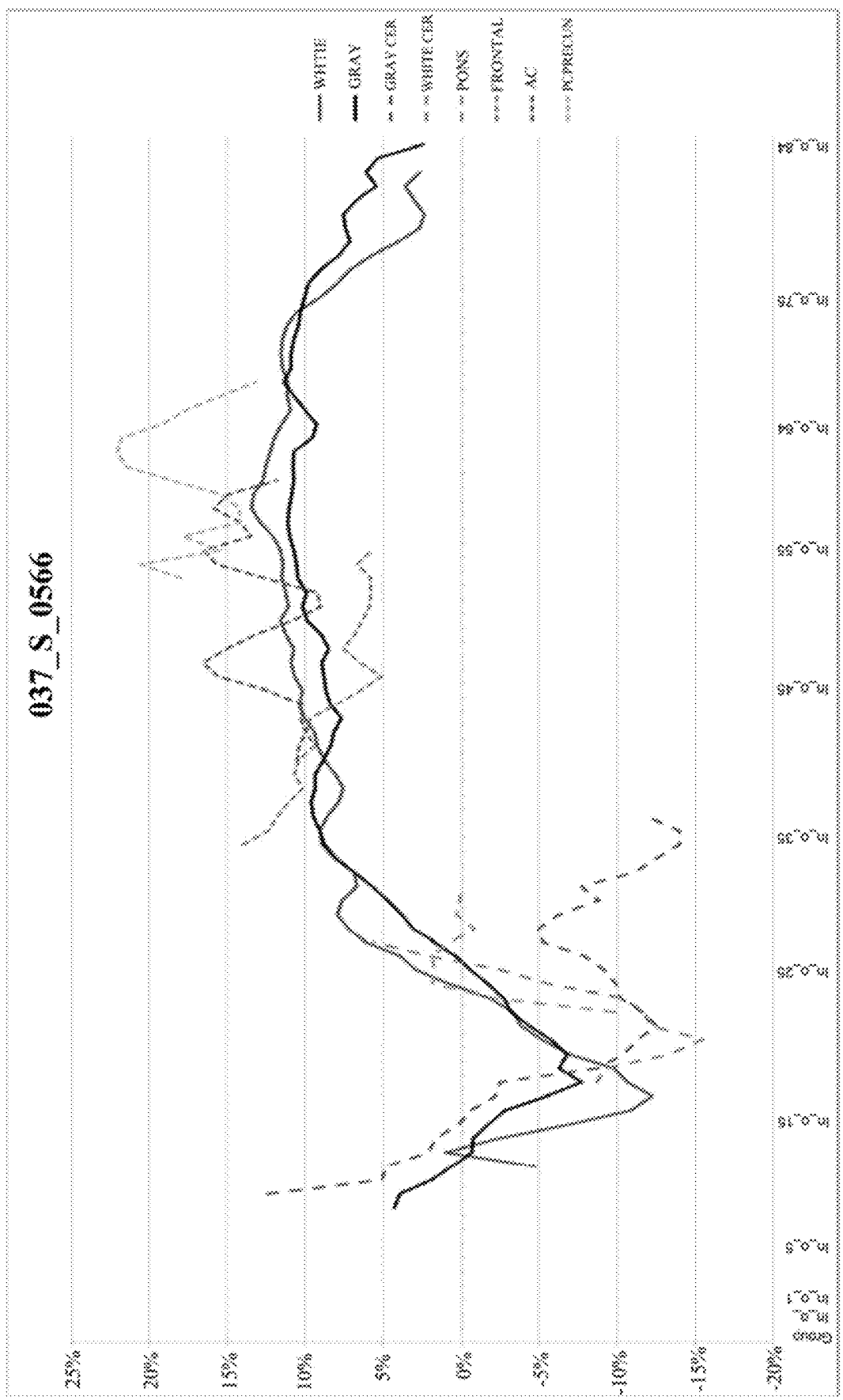
FIG. 13 shows additional VOI trajectories.

FIG. 12 shows the percentage change between the two longitudinal scans for those VOIs and reference regions. Rather than distilling these into static percentages covering several slices for each VOI, the examination was performed on a slice-by-slice basis to see how they vary across the brain. From FIG. 12, it was seen that the percentage change in cerebellum was nowhere near (i.e., at least 15% more negative than) the percentage change for other "stable" regions such as white matter and CSF, traversing through the brain, nor for gray matter overall. Therefore, any SUVRs referenced to gray cerebellum would show artificially as an increase, just because the cerebellum change was not keeping pace with that of other parts of the brain. This was also the case with pons. The fact that white, CSF and gray have all moved in the same curvilinear trajectory implies that this is not just amyloid buildup in gray matter, nor spillover from white to gray or gray to white (spillover is caused by the lower resolution of the PET scanner, whereby white and gray boundaries become blurred, as well as actual positron travel to other tissue). It is also of note that the trajectory of white, gray, and CSF is not flat, indicating the utility of applying a slice-by-slice or localized approach to the reference. Slice-by-slice measures of various VOIs, such as anterior cingulate (AC), posterior cingulate-precuneus (PCC), and frontal cortex (FRONTAL), were then "layered on," as shown in FIG. 13.

The following was obtained upon calculating and comparing the percentage changes using different reference regions ("standard" gray cerebellum and pons vs. slice-by-slice white, gray, and an amyloid poor gray mask):

|  | REF REGION: | | | | |
|---|---|---|---|---|---|
|  | WHITE | WHITE-CO | GRAY AmPoor | GRAYCER | PONS |
| AC | 2% | 2% | 1% | 20% | 13% |
| PCC | 5% | 6% | 4% | 25% | 18% |
| Frontal | −2% | −2% | −3% | 15% | 9% |

It was seen that while gray cerebellum (GRAYCER) and pons show large increases, the changes relative to white, a subregion of white (CO=centrum ovale), and Gray amyloid poor mask are much lower and in line with known amyloid accumulation rates. This was prior to refinement of the amyloid poor mask.

Example 2

Imaged at Baseline and 24 Months with Florbetapir

Longitudinal percent change for this subject showed large increases in cerebellum and pons, not matched by subcortical white matter as a reference, as shown in the table below.

| Clinical diagnosis at baseline | MCI |
|---|---|
| Scanner | Siemens Biograph 1093/94 |
| Baseline cortical ave SUVR | 1.71 |
| | 24 m change in Cortical Ave SUVR |
| Gray cerebellum | 19% |
| Whole cerebellum | 17% |
| White cer and pons | 10% |
| Pons | 11% |
| Centrum Ovale | 1% |
| Sensorimotor | 2% |

Figure 14:
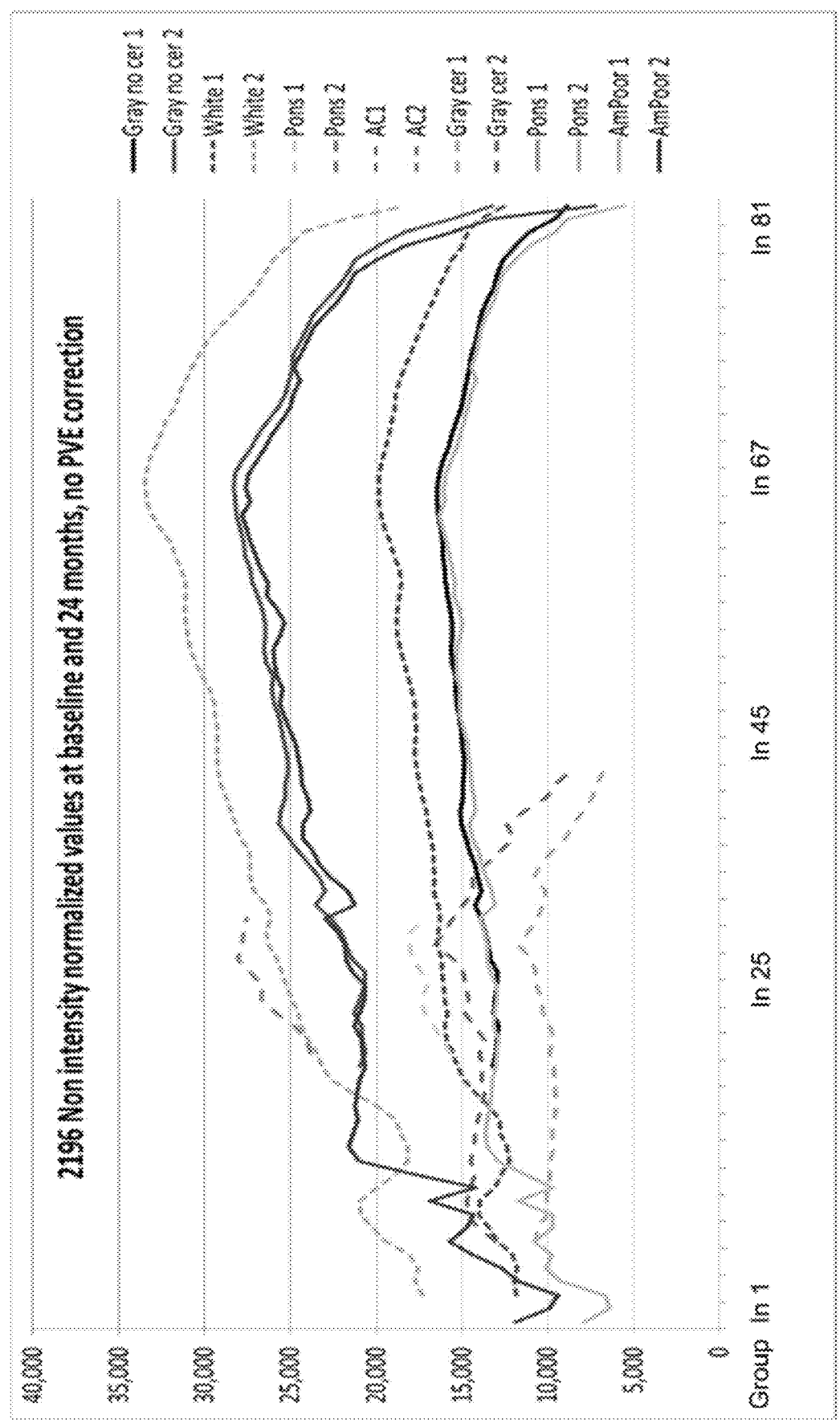
FIG. 14 shows non-intensity normalized values at baseline and 24 m.
Figure 15:
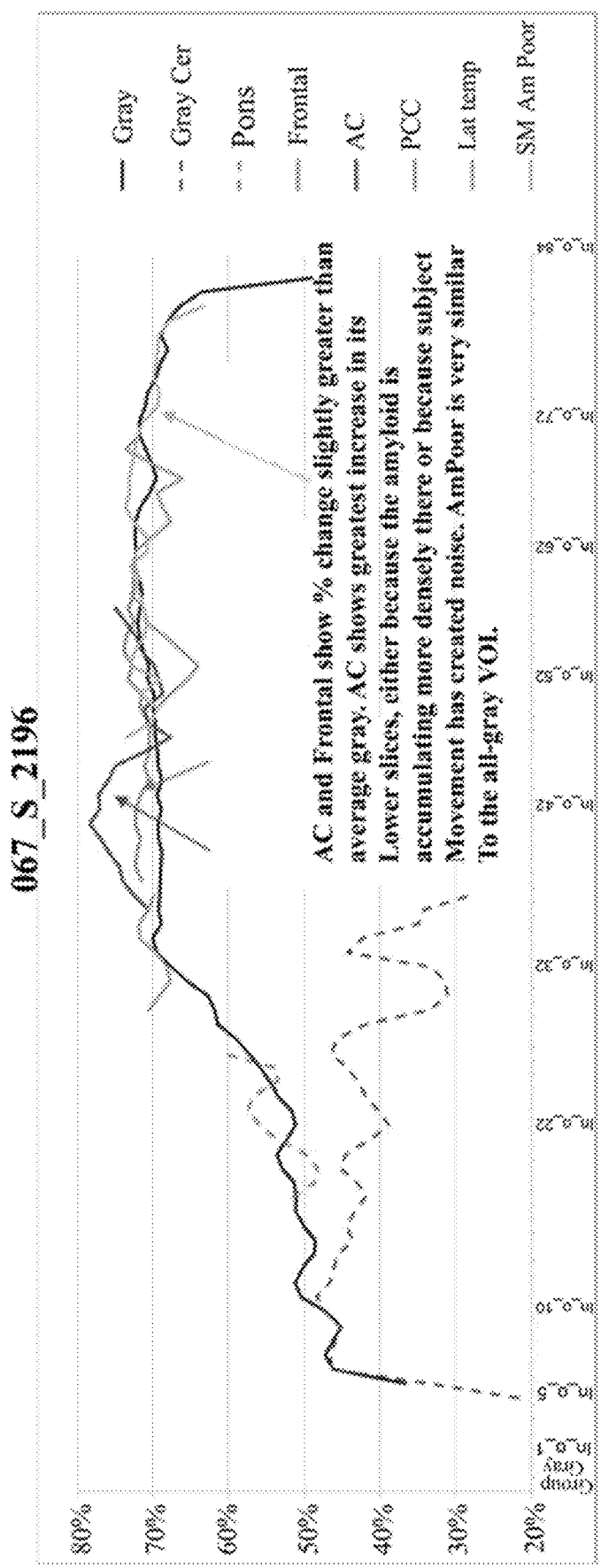
FIG. 15 shows percent change in selected reference regions and VOIs in subject 2196 between two scans.
Figure 16:
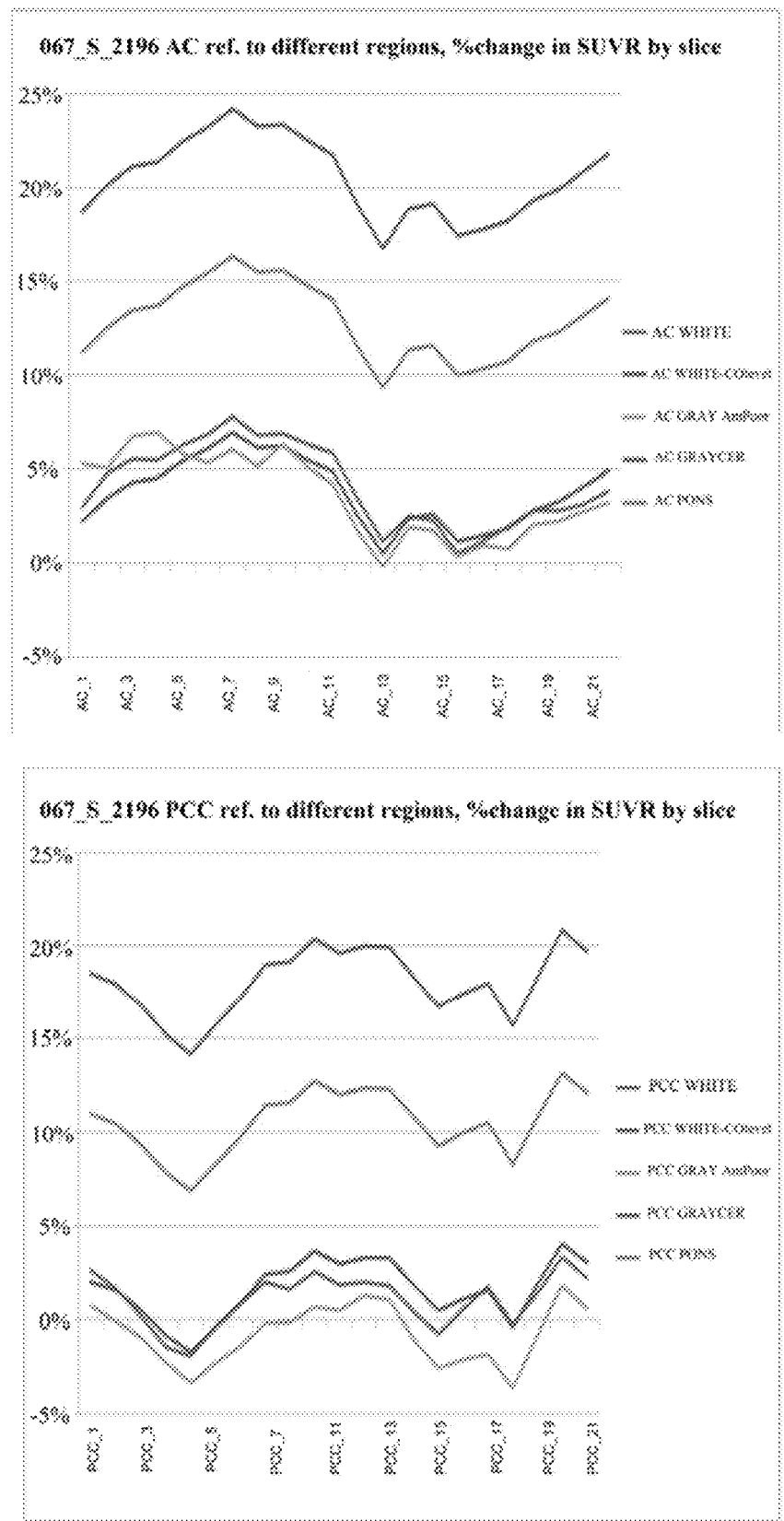
FIG. 16 shows percent change, slice-by-slice, of AC and PCC using different reference region approaches.

The slice-by-slice measures of raw values are shown in FIG. 14, and the percent changes for each non intensity normalized region are then shown in FIG. 15. It was seen that the % changes in cerebellum and also in pons are far less than that gray matter, even in amyloid poor regions. By using amyloid poor gray matter, a much less artifactual measure of change can be obtained, as compared to if cerebellum was used. Indeed, as shown in FIG. 16, the 24 month percent change when using regions other than cerebellum or pons are lower, aligned with observed amyloid accumulation rates, and also more valid based upon the survey of the entire brain profile in FIG. 15.

Example 3

This subject showed the largest increases among over 80 subjects imaged with florbetapir when VOIs were referenced to cerebellum (gray or whole). However, values referenced to pons showed minimal increases, and values referenced to subcortical white matter showed negative change (decreases). Using conventional methods, the industry would say only that "x" looks better, or more realistic, or that this subject is "an outlier."

| Clinical diagnosis at baseline | MCI (converted to AD) |
|---|---|
| Scanner | Siemens HR+ |
| Baseline Cortical Ave. SUVR | 1.09 |
| | 24 m % change in Cortical Ave SUVR |
| Gray cer | 36% |
| Whole Cer | 26% |
| White Cer and pons | 1% |
| Pons | −5% |
| Centrum Ovale | −9% |
| Sensorimotor | 6% |

Figure 17:
FIG. 17 shows non-intensity normalized values at baseline and 24 months.
Figure 18:
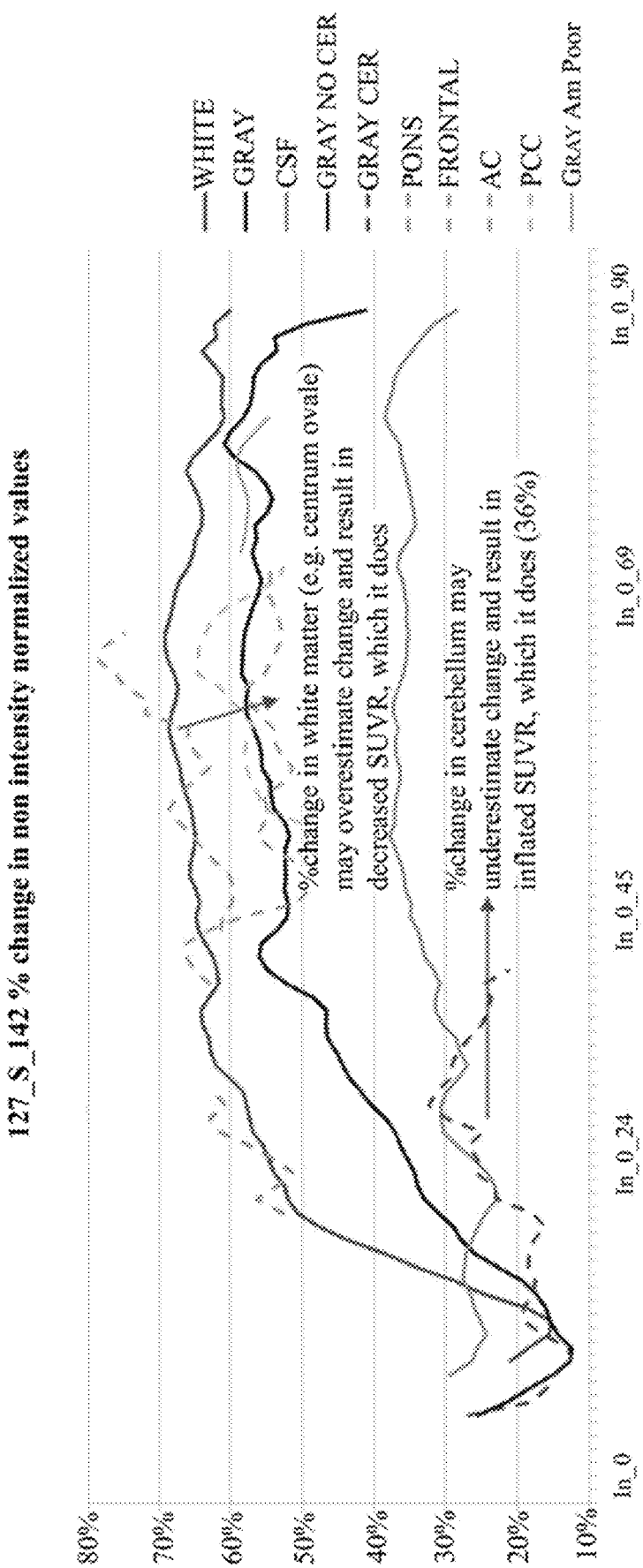
FIG. 18 shows percent change in various reference regions and VOIs.

FIG. 17 shows the raw non-intensity normalized values for several reference regions and VOIs, while FIG. 18 shows the percent change in each of those regions over 24 months.

Figure 19:
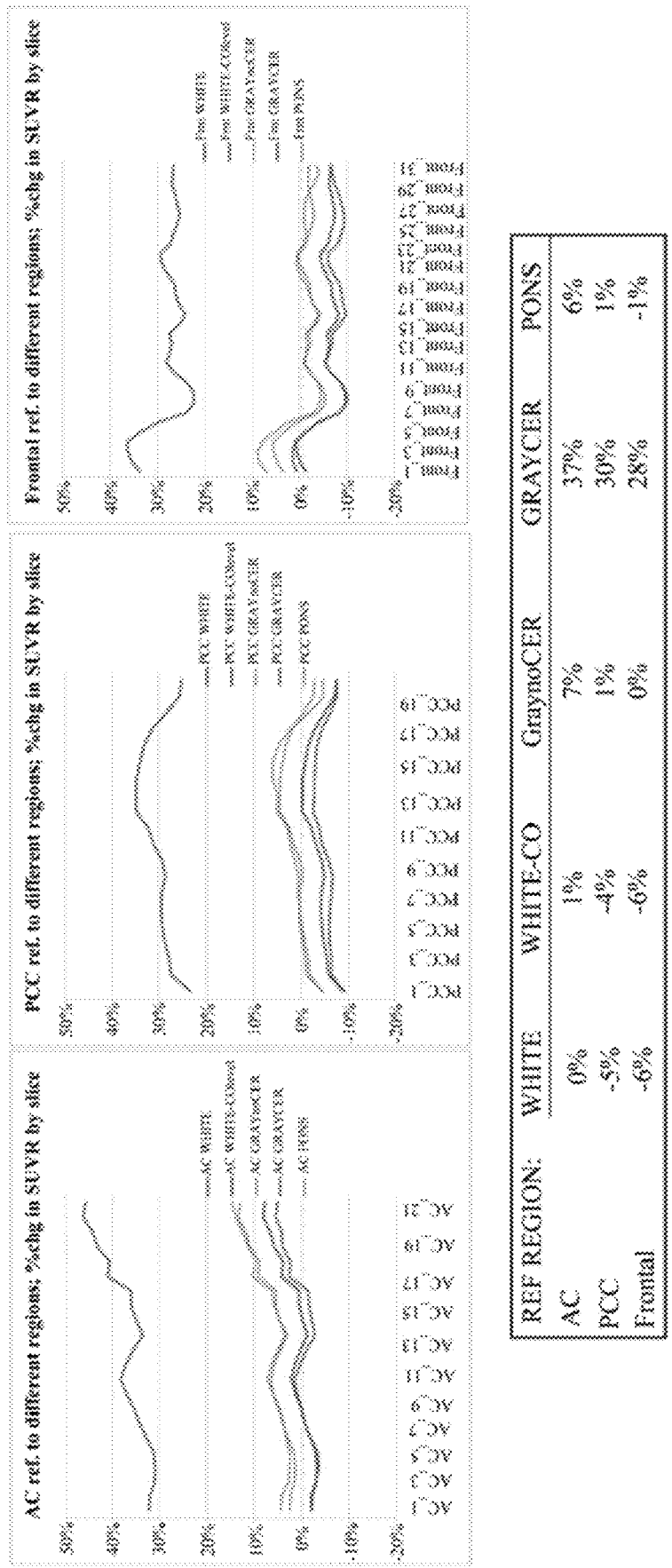
FIG. 19 shows a slice-by-slice profile, according to one embodiment of this invention.
Figure 20A:
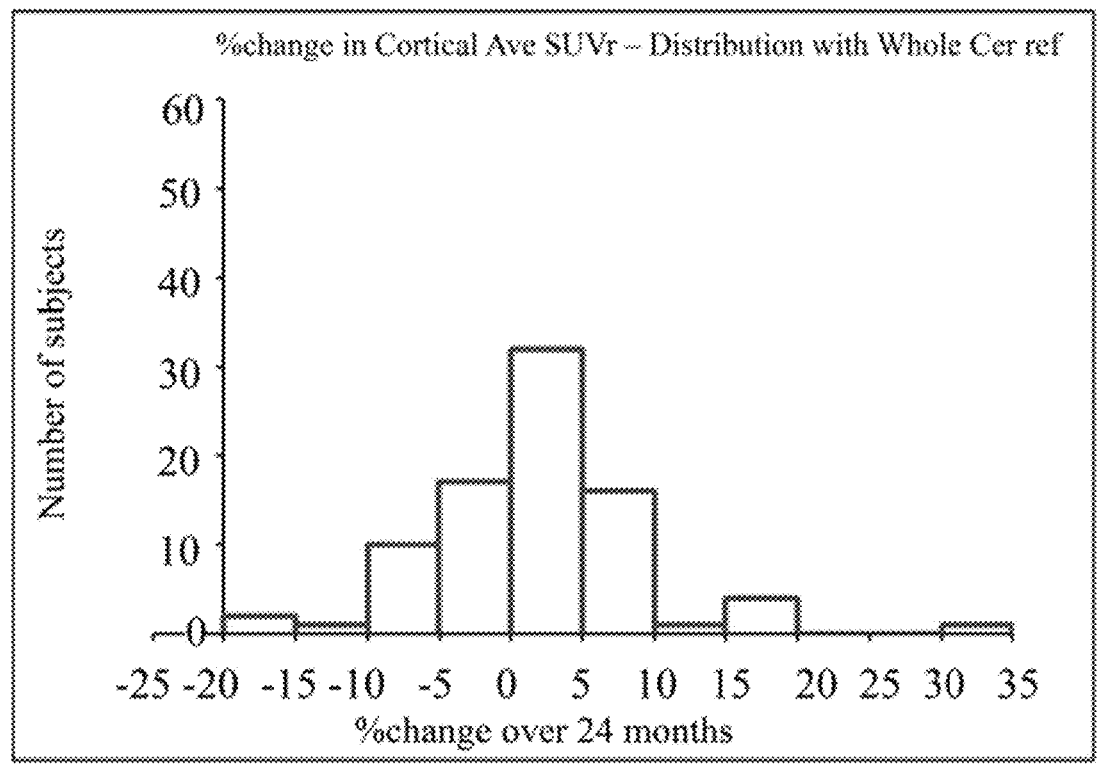
FIGS. 20A-E show the distribution in percentage change for five different reference regions: average whole cerebellum, average gray cerebellum, average pons, slice-by-slice white matter, and slice-by-slice amyloid poor gray matter
Figure 20B:
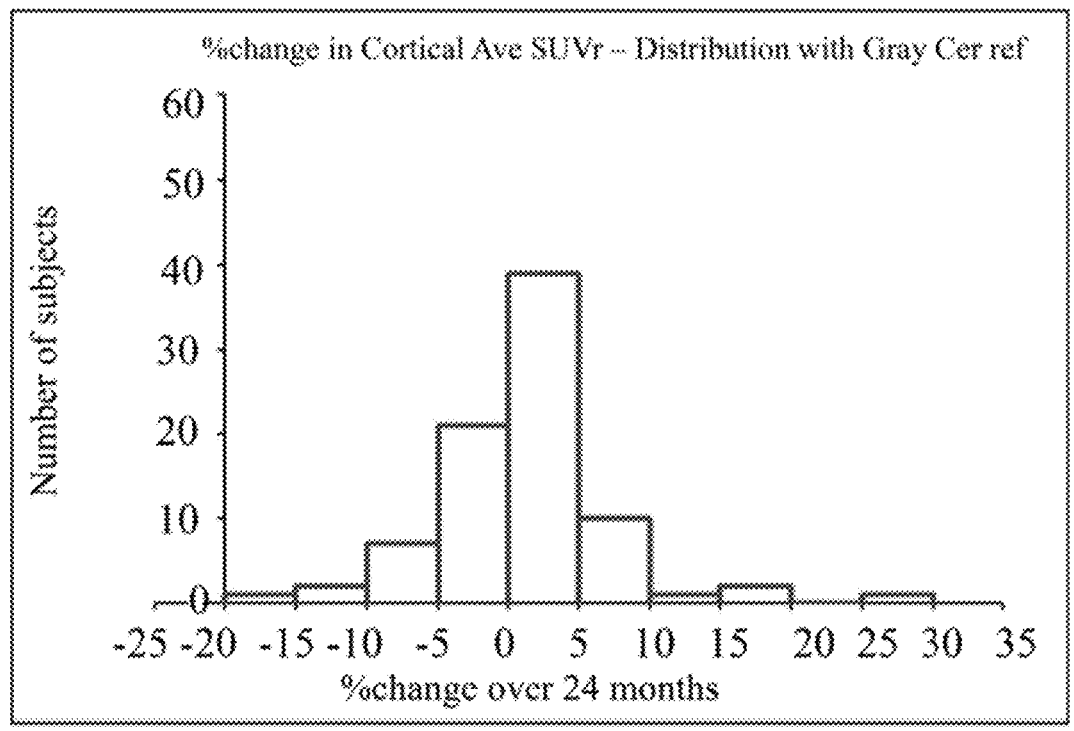
Figure 20C:
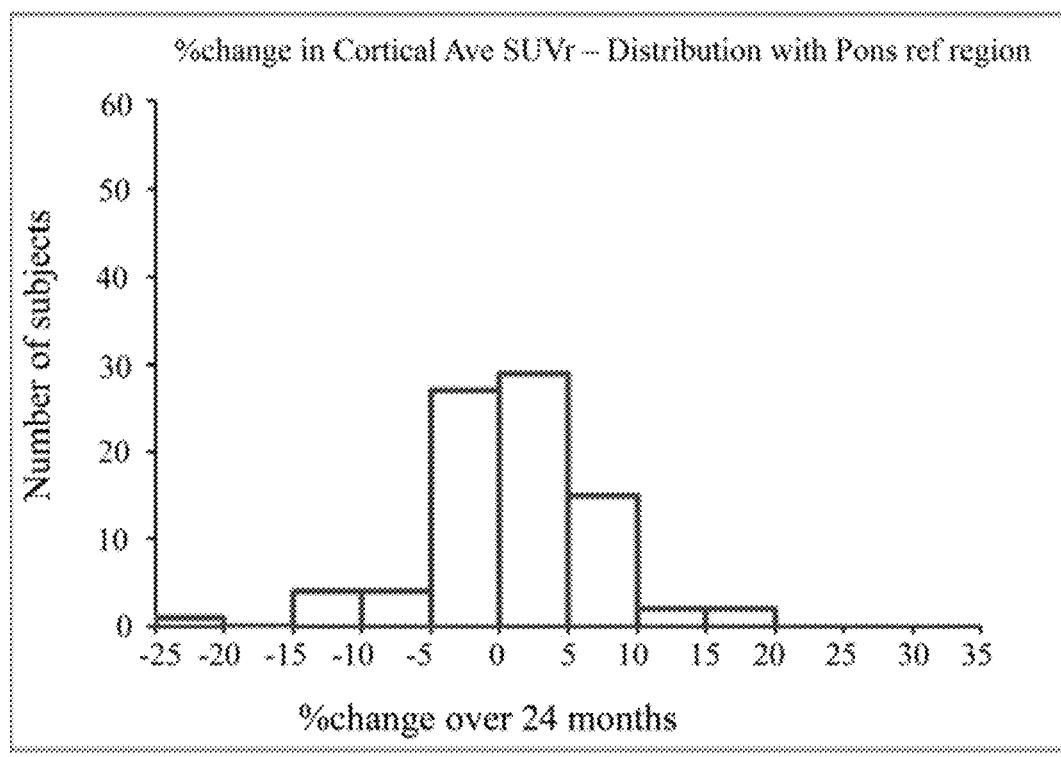
Figure 20D:
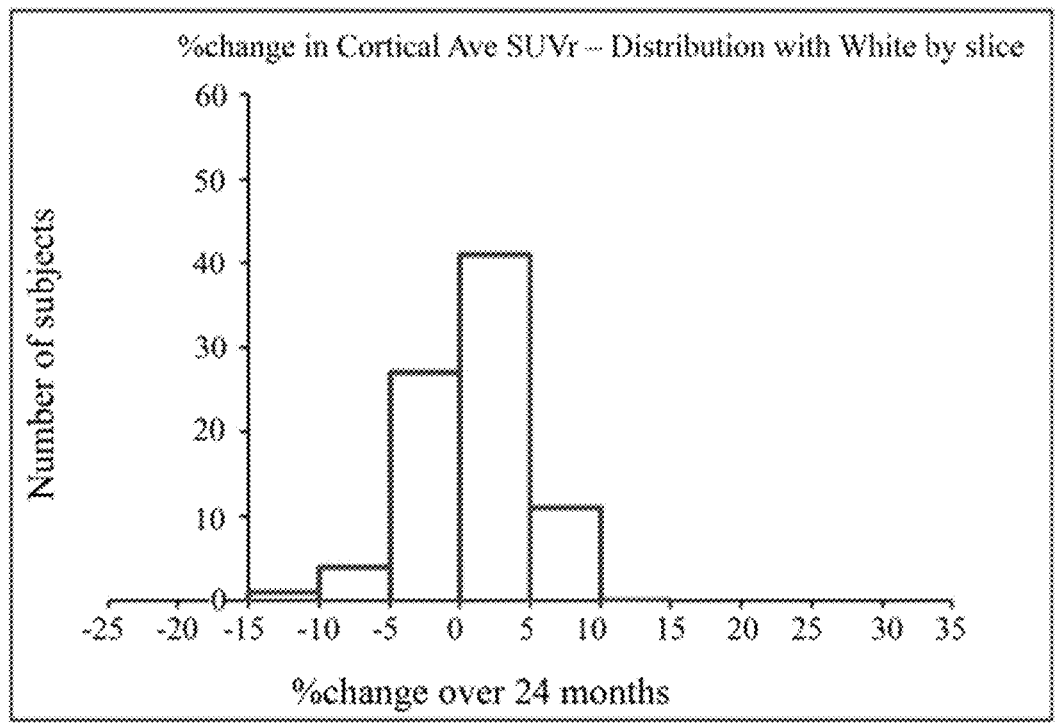
Figure 20E:
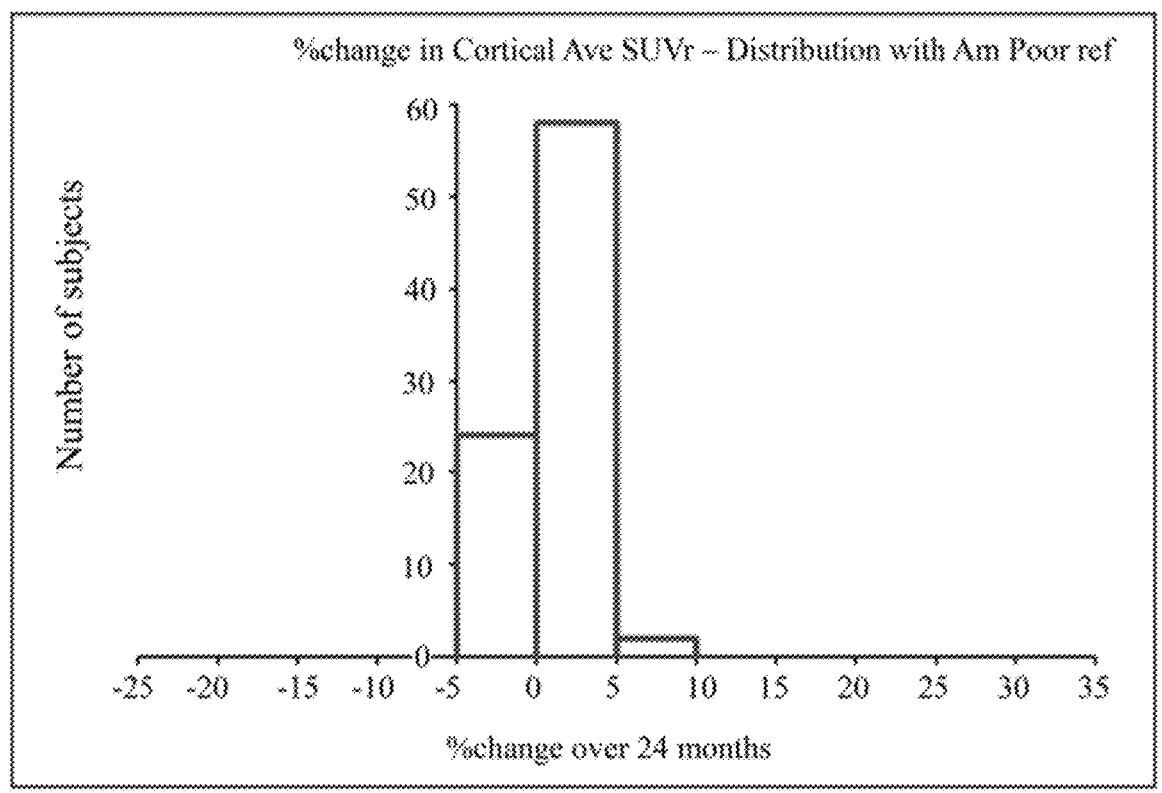

As described in FIG. 19, examining the slice-by-slice profile of the cerebellum would inflate change of other regions, whereas white matter would depress (cause to appear to decrease) changes. In this case, picking one of cerebellum, pans, or white matter will not be accurate. Using a combination may approximate the actual reference that should be used but is a guessing game of sorts. Rather, confirming which reference regions are or are not valid, and why, and identifying the amyloid poor "floor" that is best used as a reference at various points in the brain is a more insightful approach. Demonstrated below is the calculation of the percent change in SUVRs for three different VOIs, using different reference regions.

In particular embodiments of this invention it can be important to examine regional changes in light of the detected and reconstructed signal characteristics as they may vary across the brain, whether due to vulnerability to scatter and edge effects, axial FOV profile, changes in tracer clearance rates, or other factors. This allows characterization of the influence of major changes, on top of which measurement of small changes can be further enhanced through other means. In one implementation, a slice-by-slice reference region(s) is created that accommodates the changing profile of the brain within amyloid stable tissue, and used as the denominator for the VOIs in similar locales (e.g., by using the reference value in a particular slice as the denominator for the SUVR for the VOI in that same brain slice). This approach reveals for any longitudinal scans why various reference regions do or do not reliably reflect the change in signal in gray tissue throughout the brain, and in addition, allows the more accurate measurement of changes that occur in amyloid burden.

In one embodiment, gray and white tissue is characterized (e.g., measure the average signal intensity) at each slice, as well as "amyloid resistant" gray and white eroded from gray, and gray (and optionally, whole) cerebellum and pons reference regions. This provides a profile of the "carrier signal" (the amyloid resistant gray) and a measure of how well the traditional reference regions capture it throughout the brain for the scan of interest. It was found that in all cases where trajectories changed, excessive magnitude occurred, or ref regions were discordant, these diverged.

In one embodiment, an amyloid resistant gray profile is compared to overall gray, white, and CSF, and also to specific regions where amyloid may accumulate, to confirm what the stable gray reference at each slice should be. Ideally, this is done with and without PVE correction, and using slightly eroded white and CSF masks to minimize the influence of gray matter on those measured regions. Local a priori amyloid resistant gray tissue (regions known to not accumulate amyloid as quickly as other regions) can be used as a gold standard, in case subject-specific adaptive methods are not suitable for trials. This allows understanding of whether the signal is changing in all tissue throughout the brain, regardless of amyloid changes.

SUVRs of target VOIs can be measured as referenced to traditional reference regions, to slice-by-slice (i.e., locally similar) gray and white tissue, and to the amyloid resistant profile. By using a slice-by-slice approach, the method is not dependent upon the "carrier signal" being stable across superior slices, or the whole brain. The signal is interpreted in its locale, thereby compensating for a host of changes that may arise from scanner changes over time, scanner model changes, tracer kinetics, and whatever else.

The influence of white spillover and changes in white matter on amyloid poor (resistant) regions can be somewhat different than that upon amyloid rich regions, due to the increased contrast between the two (white has high binding regardless, and therefore influences amyloid poor regions more than amyloid rich regions that already have higher signal). A correction factor can thus be applied. At a minimum, the changes in VOIs that do not mask to gray matter can be compared to those that do, to test the difference (see Edison et al., *Neuroimage,* 2013, for discussion regarding different impact of white matter on gray matter depending upon whether poor or rich in amyloid).

These measurements can provide: knowledge of whether candidate reference regions such as gray cerebellum or pons changed at the same rate as other stable regions throughout the brain between two scans; knowledge of whether candidate reference regions changed at the same rate throughout, or in a variable manner over the course of several slices between two scans; a "carrier signal" against which changes between two or more scans in amyloid vulnerable regions such as frontal cortex, lateral parietal, cingulate, etc., can be measured, in their "locale"—i.e. the section of the brain in which they are located; a valid assessment of change without guessing which reference region, if any, might be correct; and/or, by assessing the absolute value profile of reference regions in comparison to that of gray, white, and CSF, and comparing to an empirically determined range of valid ratios and valid profiles across slices, within-scan stability can be assessed.

Thus, the invention provides methods for obtaining valid PET scans, and/or for evaluating the validity of a measurement of change in tracer signal between two longitudinal PET scans, obtaining measures of regional changes in tracer binding that are more accurate and reliable than those using conventional methods, and/or assessing the validity of a single scan measurement.

The methods of this invention have been applied to amyloid PET scans acquired with the radiotracer florbetapir from the Alzheimer's Disease Neuroimaging Initiative (ADNI) data set. Slice-by-slice (transaxial, coronal, and sagittal) values were calculated for regions including gray matter, white matter, cerebrospinal fluid (CSF), whole cerebellum, gray cerebellum, pons, centrum semiovale, anterior cingulate, frontal cortex, medial temporal cortex, lateral temporal cortex, posterior cingulate, precuneus, parietal cortex, and others. SUVRs were calculated for several target regions of interest using the following reference regions: average gray matter, average white matter, average whole cerebellum, average gray cerebellum, average pons, and average "amyloid poor" regions. In addition, SUVRs were calculated on a transaxial slice-by-slice basis by dividing the value of a target region, such as anterior cingulate, by the value of a reference region within the same transaxial slice, and then computing the voxel-weighted average of the SUVRs using the number of target region (such as anterior cingulate voxels in each slice) to result in a single SUVRs value. Reference regions applied in a slice-by-slice manner included gray matter, white matter, and two amyloid "poor" tissue volumes (one gray only, the other gray and white matter). The longitudinal change and percent change in SUVRs was then calculated for each subject in each region of interest, and for a cortical average region comprised of anterior cingulate, frontal cortex, posterior cingulate, precuneus, lateral temporal cortex, and parietal cortex. Longitudinal changes in amyloid negative and amyloid positive subjects, as well as in stratifications of those groups, were calculated and compared.

Longitudinal changes in cortical average SUVR in 84 ADNI-GO/2 subjects imaged with florbetapir and 70 ADNI-1 subjects imaged using 11C-PiB were examined. The following principles were considered:

SUVR=Target Region intensity/Reference Region intensity

A target region that does not change in amyloid over time will only have an unchanging SUVR if the reference region intensity changes over time by the same % as the target region Most SUVR analyses have used reference regions such as cerebellum or pons. It was hypothesized that signal changes may be different in the inferior planes encompassing these regions compared to planes closer to the center of the axial field of view due to factors including scanner detector performance and scatter correction. This could produce noise in longitudinal SUVRs unrelated to actual amyloid changes.

The way in which signal varied in several regions while traversing transaxial brain slices was first evaluated. Then we explored whether more centrally located regions that should not accumulate amyloid could serve as alternate references, reducing inferior slice variability.

Longitudinal amyloid PET scans were co-registered to the baseline PET scan; PET scans were not intensity normalized in order evaluate raw values. Using Statistical Parametric Mapping (SPM5), each subject's baseline MRI was co-registered to their corresponding baseline 11C-PiB or AV-45 scans. Template regions-of-interest were used to generate target region of interest masks (frontal, anterior cingulate, posterior cingulate-precuneus, parietal, and lateral temporal cortices, averaged to create average cortical value). Template reference regions were defined, including: gray cerebellum, whole cerebellum, pons, and a novel gray matter region (AltGM) comprised of tissue less likely to accumulate amyloid based upon published studies and SPM analyses of ADNI image data, such as motor cortex. A white matter reference (WM) was also created using each subject's individual white matter segment. Both alternate reference regions (AltGM, WM) were located in transaxial proximity to target regions, rather than in lower or uppermost slices.

Signal activity for the same type of tissue, and the same region, changed differently from slice to slice, particularly in the transaxial direction, and particularly in the lowest and uppermost slices. This was the case even in those regions that arguably accumulate little amyloid. In particular, longitudinal intensity percentage changes in cerebellum and pons raw signal differed by slice and from one another as well as from more superior target regions that typically do not accumulate amyloid. These findings remained consistent even when correcting for Partial Volume Effects and smoothing.

The 24 month change in florbetapir SUVR was similar across all references (1-2%), but variability was substantially reduced using alternate references (AltGM −3 to 6%, WM −11 to 9%) compared to gray cerebellum (−19% to 34%), whole cerebellum (−16% to 28%), and pons (−20% to 18%). Similarly, 12 month % change in 11C-PiB SUVRs was 1-3% across all references but variability was reduced with alternate references compared to gray cerebellum and pons.

FIGS. 20A-E show the distribution in percentage change for five different reference regions: average whole cerebellum, average gray cerebellum, average pons, slice-by-slice white matter, and slice-by-slice amyloid poor gray matter. It can be seen that the variability is far less for the amyloid poor gray matter, followed by white matter.

Longitudinal 24 month change in cortical average SUVR in 37 amyloid+florbetapir subjects reached significance when using the alternate references (AltGM $p<0.00009$, WM $p<0.002$). Results were similar in 11C-PiB subjects (Alt refs $p<0.00002$). Fewer directional changes were observed when using alternate reference regions.

Figure 21:
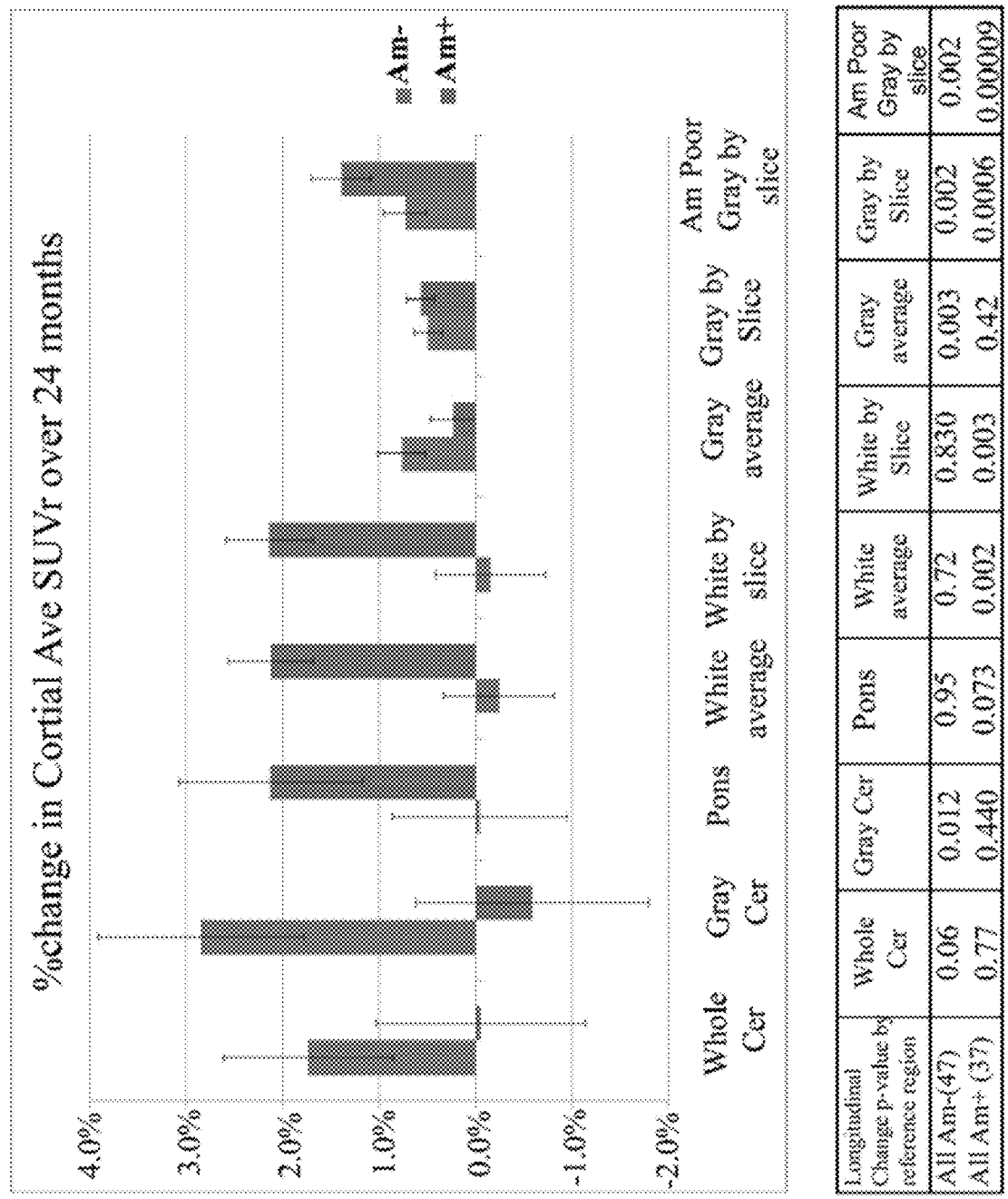
FIGS. 21 and 22 show the measured longitudinal change in cortical average SUVR for amyloid positive and negative subjects, and subgroups based upon amyloid burden for each subject at baseline.
Figure 22:
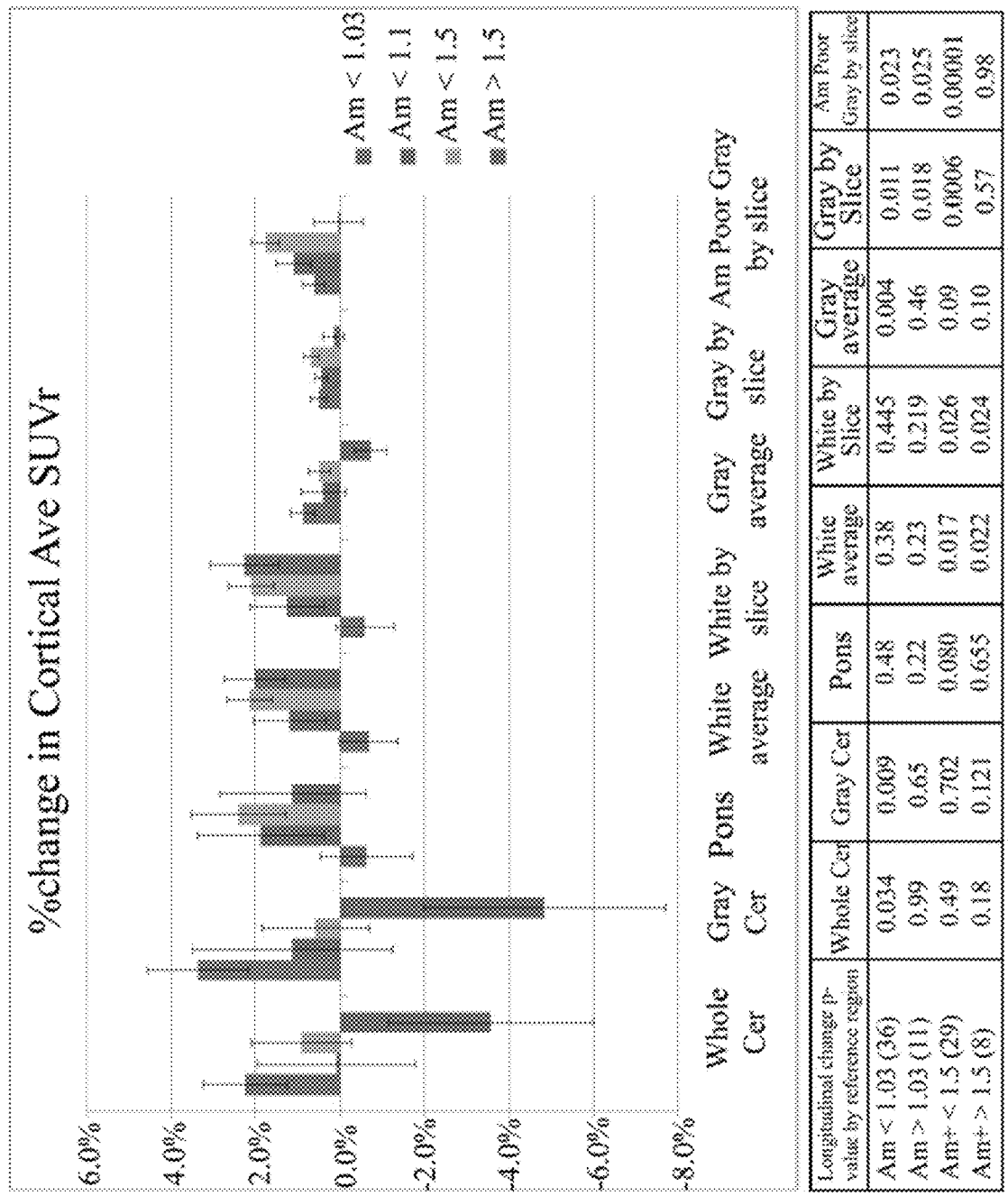

The measured longitudinal change in cortical average SUVRs is shown in the graphs of FIGS. 21 and 22 for amyloid positive and negative subjects, and subgroups based upon amyloid burden for each subject at baseline. The significance associated with the longitudinal change within group is then shown for each reference region approach.

Here it is seen that the statistical power of the amyloid poor and slice-by-slice approaches in general are superior to conventional methods.

This data further supports the benefit of the novel approaches described herein. Application of this is important to current clinical trials, and will continue to be critical to clinical trials that study subjects to assess whether accumulation of certain pathological entities such as amyloid burden has been impacted by candidate therapeutics.

Finally, the slice-by-slice approach has been applied to evaluate the stability of a single scan. It was found that the profile of the cerebellar, pons, and other candidate reference regions, both taken alone and as compared to other amyloid poor regions such as medial temporal cortex, is indicative of stability within the single scan. This can be applied to verify whether a diagnostic scan or scan used at baseline for subject inclusion in a trial is reliable.

Thus the invention provides for a method and apparatus and/or software that analyzes and/or corrects measurement variability across a scanner field of view within an image scan. The method, implemented through an imaging system, identifies and negates scan inconsistencies across the scanner field of view. The method enables assessment of reference region validity and reduces variability, thereby increasing statistical power and improving the feasibility of longitudinal measurement. The approach also addresses variability due to scanner changes, reduces erratic trajectories, and explains the erratic trajectories that may be found using past reference volume approaches.

The invention illustratively disclosed herein suitably may be practiced in the absence of any element, part, step, component, or ingredient which is not specifically disclosed herein.

While in the foregoing detailed description this invention has been described in relation to certain preferred embodiments thereof, and many details have been set forth for purposes of illustration, it will be apparent to those skilled in the art that the invention is susceptible to additional embodiments and that certain of the details described herein can be varied considerably without departing from the basic principles of the invention.

What is claimed is:

1. A method for correcting image measurement variability across a scanner field of view within an image scan of an imaging device, the method comprising:
    providing the image scan, wherein the image scan comprises image slices of a tissue;
    identifying and negating scan inconsistencies in the image scan across the scanner field of view by a data processor mathematically adjusting values across the image slices relative to a reference signal, wherein the reference signal is obtained from one or more reference regions of a patient tissue within the image scan;
    calibrating by comparing two scans of the patient tissue and measuring and comparing imaging agent signals in each of a predetermined reference region of imaging agent uptake and one or more predetermined interest regions having a higher imaging agent uptake than the predetermined reference region across corresponding slices of the two scans; and
    for each of the predetermined reference region of imaging agent uptake and the predetermined region having the higher imaging agent uptake between the slices, reconciling signals by determining a transform value from a bias and slope of an equation that translates signals of a first of the two scans to signals of a second of the two scans, and applying the transform value to all slices of the second of the two scans.

2. The method according to claim 1, further comprising:
    normalizing values across the image scan as a function of reference signals across the image scan and measured across the field of view.

3. The method according to claim 2, further comprising adjusting measured signals in the image scan by multiplying each of the measured signals by an adjustment value provided by the reference signal.

4. The method according to claim 1, wherein the predetermined reference region comprises a tissue volume that is resistant to accumulation of the imaging agent.

5. The method according to claim 1, wherein the predetermined reference region comprises white matter brain tissue.

6. The method according to claim 1, wherein the predetermined reference region is a predetermined non-specific binding region for the imaging agent.

7. A non-transitory recordable medium including encoded instructions on a recordable medium for automatically executing steps according to claim 1.

8. A method for correcting image measurement variability across a scanner field of view within an image scan of an imaging device, the method comprising:
    providing the image scan, wherein the image scan comprises image slices of a tissue;
    identifying and negating scan inconsistencies in the image scan across the scanner field of view by a data processor mathematically adjusting values across the image slices relative to a reference signal, wherein the reference signal is obtained from one or more reference regions of a patient tissue within the image scan;
    calibrating by comparing two scans of the patient tissue and measuring and comparing imaging agent signals in each of a predetermined reference region of imaging agent uptake and one or more predetermined interest regions having a higher imaging agent uptake than the predetermined reference region across corresponding slices of the two scans; and
    comparing signal curves of the predetermined reference region of imaging agent uptake and the predetermined region having the higher imaging agent uptake to determine a transform value from a bias and slope of an equation as a reconciliation of the predetermined reference region of imaging agent uptake and the predetermined region having higher imaging agent uptake of each of the two scans to the other of the two scans, wherein a percent deviation between resulting adjusted values between the two scans are calculated on a slice by slice basis, and determined to be within or not of a threshold value indicating that shape profiles of the two scans reflect measurement of a same tissue.

9. The method according to claim 8, wherein the predetermined reference region comprises a tissue volume that is resistant to accumulation of the imaging agent.

10. The method according to claim 8, wherein the predetermined reference region comprises white matter brain tissue.

11. The method according to claim 8, wherein the predetermined reference region is a predetermined non-specific binding region for the imaging agent.

12. A non-transitory recordable medium including encoded instructions on a recordable medium for automatically executing steps according to claim 8.

13. A method for correcting image measurement variability across a scanner field of view within an image scan of an imaging device, the method comprising:
 providing the image scan, wherein the image scan comprises image slices of a tissue;
 identifying and negating scan inconsistencies in the image scan across the scanner field of view by a data processor mathematically adjusting values across the image slices relative to a reference signal, wherein the reference signal is obtained from one or more reference regions of a patient tissue within the image scan;
 calibrating by comparing two scans of the patient tissue and measuring and comparing imaging agent signals in each of a predetermined reference region of imaging agent uptake and one or more predetermined interest regions having a higher imaging agent uptake than the predetermined reference region across corresponding slices of the two scans; and
 calculating a percent change for each signal of two scans across the field of view, preparing a signal curve for the percent change across the field of view, and determining subject movement or scanner detection change from a deviation between the prepared signal curves.

14. The method according to claim 13, wherein the predetermined reference region comprises a tissue volume that is resistant to accumulation of the imaging agent.

15. The method according to claim 13, wherein the predetermined reference region comprises white matter brain tissue.

16. The method according to claim 13, wherein the predetermined reference region is a predetermined non-specific binding region for the imaging agent.

17. A non-transitory recordable medium including encoded instructions on a recordable medium for automatically executing steps according to claim 13.

18. A method for correcting image measurement variability across a scanner field of view within an image scan of an imaging device, the method comprising:
 providing the image scan, wherein the image scan comprises image slices of a tissue;
 identifying and negating scan inconsistencies in the image scan across the scanner field of view by a data processor mathematically adjusting values across the image slices relative to a reference signal, wherein the reference signal is obtained from reference regions of a patient tissue within the image scan; and
 calibrating by comparing two scans of the patient tissue and measuring and comparing imaging agent signals in each of a predetermined reference region of imaging agent uptake and one or more predetermined interest regions having a higher imaging agent uptake than the reference region across corresponding slices of the two scans,
 wherein a selected tissue region is measured through a plurality of slices and further comprising determining a validity of one or more measured signal of the tissue region by comparing each measured signal across the plurality of slices to a predetermined range of values.

19. The method according to claim 18, wherein the predetermined reference region comprises a tissue volume that is resistant to accumulation of the imaging agent.

20. The method according to claim 18, wherein the predetermined reference region comprises white matter brain tissue.

21. The method according to claim 18, wherein the predetermined reference region is a predetermined non-specific binding region for the imaging agent.

22. A non-transitory recordable medium including encoded instructions on a recordable medium for automatically executing steps according to claim 18.

* * * * *